United States Patent
Montesinos Seguí et al.

(10) Patent No.: US 10,548,325 B2
(45) Date of Patent: Feb. 4, 2020

(54) STRAIN OF BACILLUS AMYLOLIQUEFACIENS AND ITS USE IN THE CONTROL OF DISEASES CAUSED BY BACTERIA AND FUNGI IN PLANTS

(71) Applicant: INDUSTRIAS QUÍMICAS DEL VALLÉS, S.A., Mollet del Vallès (ES)

(72) Inventors: Emilio Montesinos Seguí, Banyoles (ES); Isabel Mora Pons, Girona (ES); Jordi Cabrefiga Olamendi, Girona (ES)

(73) Assignee: INDUSTRIAS QUÍMICAS DEL VALLÉS, S.A., Mollet del Vallès (ES)

( * ) Notice: Subject to any disclaimer, the term of this patent is extended or adjusted under 35 U.S.C. 154(b) by 0 days.

(21) Appl. No.: 15/561,481

(22) PCT Filed: Mar. 23, 2016

(86) PCT No.: PCT/EP2016/056451
§ 371 (c)(1),
(2) Date: Sep. 25, 2017

(87) PCT Pub. No.: WO2016/156164
PCT Pub. Date: Oct. 6, 2016

(65) Prior Publication Data
US 2018/0049443 A1    Feb. 22, 2018

(30) Foreign Application Priority Data
Mar. 27, 2015   (ES) .................... 201530415

(51) Int. Cl.
*A01N 63/00* (2006.01)
*C12R 1/07* (2006.01)

(52) U.S. Cl.
CPC ............... *A01N 63/00* (2013.01); *C12R 1/07* (2013.01)

(58) Field of Classification Search
CPC .................................................. A01N 63/00
See application file for complete search history.

(56) References Cited

U.S. PATENT DOCUMENTS

| | | |
|---|---|---|
| 2008/0102062 A1 | 5/2008 | Kim et al. |
| 2010/0143316 A1 | 6/2010 | Hsieh et al. |
| 2011/0230345 A1 | 9/2011 | Snyder et al. |

FOREIGN PATENT DOCUMENTS

| | | |
|---|---|---|
| WO | WO 2013/034940 A2 | 3/2013 |
| WO | WO 2014/178032 A1 | 11/2014 |

OTHER PUBLICATIONS

International Search Report and Written Opinion dated Jun. 14, 2016 for PCT/EP2016/056451, 14 pages.

Almoneafy, Abdulwareth A., et al., "Tomato plant growth promotion and antibacterial related-mechanisms of four rhizobacterial *Bacillus* strains against *Ralstonia solanacearum*", Symbiosis 2014, vol. 63, pp. 59-70, DOI:10.1007/S13199-014-0288-9, ISSN 0334-5114, XP035397342.

Arguelles-Arias, Anthony, et al., "Bacillus amyloliquefaciens GA1 as a source of potent antibiotics and other secondary metabolites for biocontrol of plant pathogens", Nov. 26, 2009, Microbial Cell Factories. vol. 8, No. 63, pp. 1-12.

Cabrefiga, Jordi, et al., "Analysis of aggressiveness of *Erwinia amylovora* using disease-dose and time relationships", Aug. 10, 2005, Phytopathology, vol. 95, pp. 1430-1437.

Chen, Xiao Hua, et al., "Comparative analysis of the complete genome sequence of the plant growth-promoting bacterium *Bacillus amyloliquefaciens* FZB42", Nature Biotechnology, Aug. 19, 2007, vol. 25, No. 9, pp. 1007-1014.

Chen, Xiao-Hua, et al., "More than anticipated—production of antibiotics and other secondary metabolites by *Bacillus amyloliquefaciens* FZB42", Journal of Molecular Microbiology and Biotechnology 2009, vol. 16, pp. 14-24, No. 1-2, DOI:10.1159/000142891, XP009127778.

Daffonchio, Daniele, et al., "PCR fingerprinting of whole genomes: the spacers between the 16S and 23s rRNA genes and of intergenic tRNA gene regions reveal a different intraspecific genomic variability of *Bacillus cereus* and *Bacillus licheniformis*", 1998, International Journal of Systematic Bacteriology, vol. 48, pp. 107-116.

Koumoutsi, Alexandra, et al., "Structural and Functional Characterization of Gene Clusters Directing Nonribosomal Synthesis of Bioactive Cyclic Lipopeptides in *Bacillus amyloliquefaciens* Strain FZB42", Feb. 2004, Journal of Bacteriology, vol. 186, No. 4, pp. 1084-1096.

Landa, Blanca B., et al., Integrated management of Fusarium wilt of chickpea with sowing date, host resistance, and biological control, Apr. 29, 2004, Phytopathology, vol. 94, pp. 946-960.

(Continued)

*Primary Examiner* — Albert M Navarro
*Assistant Examiner* — Mark Navarro
(74) *Attorney, Agent, or Firm* — Squire Patton & Boggs (US) LLP

(57) ABSTRACT

The present invention refers to the strain CECT8836 of *Bacillus amyloliquefaciens* and mutants thereof, and the use of said strain as a pesticide in controlling plant diseases caused by fungi and bacteria. Further aspects of the invention relate to methods for preparing suspensions and extracts of the strain CECT8836 of *B. amyloliquefaciens*, pesticidal compositions comprising said strain and an extract of CECT8836 of *B. amyloliquefaciens* with antimicrobial activity. Finally the invention relates to a method for the biological control of various plant diseases caused by fungi and bacteria both in vegetable plants and in fruit trees, comprising treating these plants with the strain CECT8836 of *B. amyloliquefaciens*, a composition including it or a cell-free extract derived from CECT8836 of *B. amyloliquefaciens*.

17 Claims, 11 Drawing Sheets
Specification includes a Sequence Listing.

(56) References Cited

OTHER PUBLICATIONS

Lee, Ki Seog, et al., "Structure of a protein-DNA complex essential for DNA protection in spores of *Bacillus* species", Feb. 26, 2008, Proceedings of the National Academy of Sciences of the United States of America, vol. 105, No. 8, pp. 2806-2811.

Mora, Isabel, et al., "Antimicrobial peptide genes in *Bacillus* strains from plant environments", International Microbiology (2011), vol. 14, pp. 213-223.

Moragrega, Concepcio, et al., "Evaluation of drench treatments with phosphonate derivatives against *Pseudomonas syringae* pv. *syringae* on pear under controlled environment conditions", European Journal of Plant Pathology, 1998, vol. 104: 171-180.

Pathak, k.v., et al., "Characterization of fungal antagonistic bacilli isolated from aerial roots of banyan (*Ficus benghalensis*) using intact-cell MALDI-TOF mass spectrometry (ICMS)", Journal of Applied Microbiology, May 2013, vol. 114, No. 5, pp. 1300-1310, ISSN 1365-2672, XP002758117.

Romero, D., et al., "Isolation and evaluation of antagonistic bacteria towards the cucurbit powdery mildew fungus *Podosphaera fusca*", Sep. 16, 2003, Applied Microbiology and Biotechnology, vol. 64, pp. 263-269.

Sambrook, Joseph, et al., "Molecular Cloning: A Laboratory Manual", Chapter 13, "Mutagenesis", Cold Spring Harbor, 3rd Ed, 2001.

Lioa, et al., "Clarification of the Antagonistic Effect of the Lipopeptides Produced by Bacillus amyloliquefaciens BPD1 against *Pyricularia oryzae* via In Situ MALDI-TOF IMS Analysis", www.mdpi.com/journal/molecules, Molecules 2016, 21, 1670; doi:10.3390/molecules21121670, pp. 1-11.

Emilio Montesinos and Anna Bonaterra, "Dose Response Models in Biological Control of Plant Pathogens: An Empirical Verification", The American Phytopathological Society, 1996, pp. 464-472.

Mora, et al., "Antimicrobial peptide genes in Bacillus strains from plant environments", International Microbiology, vol. 14, 2011. pp. 213-223.

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
tcgggacagg aagacatcat                                            20

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
ccactcaaac ggataatcct ga                                         22

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gaatcccgtt gttctccaaa                                            20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gcgggtattg aatgcttgtt                                            20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
ggctgctgca gatgctttat                                            20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
tcgcagataa tcgcagtgag                                            20

<210> SEQ ID NO 7
<211> LENGTH: 20
<212> TYPE: DNA
<213> ORGANISM: Artificial Sequence

```
<220> FEATURE:
<223> OTHER INFORMATION: primer

<400> SEQUENCE: 7
ggcccgttct ctaaatccat                                              20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gtcatgctga cgagagcaaa                                              20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
ggtttgttgg atggagctgt                                              20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gcaaggagtc agagcaaggt                                              20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
cagctcatgg gaatgctttt                                              20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ctcggtcctg aagggacaag                                              20

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13
gcggcgtgcc taatacat                                                18
```

```
<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
taaggttctt cgcgttgctt                                                   20

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
tcaactagtt cagtatggac gaca                                              24

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
atgacagtcg cggtaaaacc                                                   20

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17
ctacggcaag gcgcagctga cg                                                22

<210> SEQ ID NO 18
<211> LENGTH: 10
<212> TYPE: DNA
<213> ORGANISM: Artificial Sequence
<220> FEATURE:
<223> OTHER INFORMATION: primer

<400> SEQUENCE: 18
ctgagacgga                                                              10

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
cgcaaaagct cttcgaccgc cgtc                                              24

<210> SEQ ID NO 20
<211> LENGTH: 24
<212> TYPE: DNA
<213> ORGANISM: Artificial Sequence
<220> FEATURE:
<223> OTHER INFORMATION: primer
```

```
<400> SEQUENCE: 20
ctctcgtgcc gtcggaatat ccgc                                              24

<210> SEQ ID NO 21
<211> LENGTH: 27
<212> TYPE: DNA
<213> ORGANISM: Artificial Sequence
<220> FEATURE:
<223> OTHER INFORMATION: primer

<400> SEQUENCE: 21
cggagtgaaa ccgtgccggg ataaaga                                           27

<210> SEQ ID NO 22
<211> LENGTH: 23
<212> TYPE: DNA
<213> ORGANISM: Artificial Sequence
<220> FEATURE:
<223> OTHER INFORMATION: primer

<400> SEQUENCE: 22
gaccattcag agcggaaagc tcc                                               23

<210> SEQ ID NO 23
<211> LENGTH: 27
<212> TYPE: DNA
<213> ORGANISM: Artificial Sequence
<220> FEATURE:
<223> OTHER INFORMATION: primer

<400> SEQUENCE: 23
ggaagaaaaa cagtcgaggc gatgctg                                           27

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
gagaagctcc gccgtcacca gtg                                               23

<210> SEQ ID NO 25
<211> LENGTH: 27
<212> TYPE: DNA
<213> ORGANISM: Artificial Sequence
<220> FEATURE:
<223> OTHER INFORMATION: primer

<400> SEQUENCE: 25
cgcctaaagt agcgccgcca tcaacgc                                           27

<210> SEQ ID NO 26
<211> LENGTH: 23
<212> TYPE: DNA
<213> ORGANISM: Artificial Sequence
<220> FEATURE:
<223> OTHER INFORMATION: primer

<400> SEQUENCE: 26
ccgcgatgga gcgggattat ccg                                               23
```

STRAIN OF *BACILLUS AMYLOLIQUEFACIENS* AND ITS USE IN THE CONTROL OF DISEASES CAUSED BY BACTERIA AND FUNGI IN PLANTS

The present invention relates to the field of phytosanitary products, specifically to a new strain of *Bacillus amyloliquefaciens* and its use in the biological control of fungal and bacterial diseases in crops of agricultural interest, especially in vegetables and pome fruit trees.

STATE OF THE ART

The impact caused by the massive use of synthetic phytosanitary products on the environment and on the health of consumers is well known. For this reason the control of plant diseases has shifted to the rational use of fungicides and bactericides, and the application of less toxic methods with less environmental impact. In this regard, there is a trend towards integrated pest management (IPM), in which different methods (physical, mechanical, chemical, biological, genetic, legal and cultural) are combined in order to achieve a good control of plant pathogenic agents, thus reducing the number of treatments to be performed. This shift in control was in part forced by a social demand for more healthy agricultural products, which has led to a new legislative framework for phytosanitary products in the European Union covered by Directive 2009/128/EC and Regulation (EC) 1107/2009 of the European Parliament and Council concerning the sustainable use and marketing of pesticides. This guideline main objective is to reduce the use of phytosanitary products and their sustainability through integrated pests, diseases, and of the environmental protection management, establishing that the phytosanitary battle means should preferably be biological and physical.

Currently, antibiotics are the phytosanitary products that show the greatest effectiveness in controlling bacterial diseases in plants. However, prolonged use of antibiotics favours the generation of resistant strains of the pathogen which is being eradicated, which limits its effectiveness. Furthermore, the emergence of antibiotic resistance in plant pathogenic bacteria can be transferred to other bacteria, including human pathogens. This fact explains the ban on the use of antibiotics in agriculture in many countries, including the European Union. An alternative to antibiotics are broad spectrum antimicrobials such as copper-based compounds, but in this case they have limited efficacy and adverse environmental impact due to their toxicity and accumulation in the environment.

In this new scenario, microbial pesticides based on microbial strains, mainly fungal and bacterial species, offer an alternative or complement to chemical pesticides. However, at present there is only a limited number of microbial pesticides, being also most of them effective in controlling fungal disease but not bacterial diseases.

Thus, the development of microbial pesticides capable of controlling bacterial disease in plants is of great interest.

Despite the efforts being made in research and development of active bacterial strains useful in the control of bacterial and fungal infections, it was found that most of these strains lead to the production of toxic secondary metabolites, lack an appropriate ecological aptitude for plant colonisation, they prove to be less effective than synthetic chemicals as well as certain unstability over time, which makes the formulation of these strains into compositions of long duration difficult.

In some cases it has been proven that bacterial strains do not colonise and survive effectively in the organs of the host to be protected, requiring the application of these strains in high concentrations or complex formulations of said strains to achieve a significant effect of disease control. Furthermore, although they are biological products having advantages over other synthesis pesticide products, the fact that they involve living organisms means that the environmental and host conditions affect their biological activity, making their effectiveness generally variable and significantly lower than the reference chemical products.

A very important aspect to consider is related to biosafety, one of the main requirements that the authorities responsible for the approval of products for human consumption, including phytosanitary products, take into account (EPA in USA, EFSA in Europe). Thus, some of the species that have been described as good biocontrol agents have been seen to be related to possible opportunistic or non opportunistic pathogenicity, as it is the case of *Pseudomonas fluorescens* and *Pantoea agglomerans* species, which have been cited as the cause of clinical infections and sepsis, which can be considered as an hindrance to the authorization of strains of these species for their use as a pesticide agent. In the EU, the strains *Pseudomonas fluorescens* A506, *Pantoea vagans* 09-1, *P. agglomerans* E325 and *P. agglomerans* P10c have not been considered as QPS (Qualified Presumption of Safety, a similar term to the known GRAS Generally Recognized As Safe).

Another important issue to be considered is the production process at industrial level. The need for products with longer shelf-life requires the preparation of these products preferably in a dehydrated form. The dehydration processes used require drying stages that significantly affect the microorganism viability, limiting the process yield, particularly in Gram-negative bacteria such as *Pseudomonas* sp. and *Pantoea* sp, which are more sensitive to thermal and dehydration treatments than the Gram-positive bacteria. In the specific case of the genus *Bacillus*, the fact that it produces spores greatly facilitates its formulation into dehydrated powder form as the loss of viability is very low, resulting in a very high yield at the end of the process.

In this regard, various strains of *Bacillus subtilis* or related species have been developed as biocontrol agents, such as the strain QST713 (Bonaterra A et al, "Prospects and Limitations of microbial biopesticides for control of bacterial and fungal pomefruit tree diseases" Trees 2012, vol. 26, pp. 215-226) and FZB42 of *B. amyloliquefaciens* species. Both strains are the active ingredient of products approved or pending approval for use as microbial pesticides. However, many of these strains show a limited activity profile, normally focused on controlling fungi.

Therefore, despite the efforts made, there still remains the need for alternative bacterial strains to those existing, which, while being effective in controlling phytopathogenic fungi, also show effectiveness in controlling infection caused by phytopathogenic bacteria and that overcome the drawbacks of the state of the art.

SUMMARY OF THE INVENTION

The inventors have isolated a new strain of the genus *Bacillus* characterised by having a broad spectrum of activity, being very efficient in controlling various bacterial and fungal pathogens. Furthermore it overcomes some of the limitations exhibited by other strains already described in the state of the art, as shown below.

Thus, in a first aspect the invention relates to a strain of *Bacillus amyloliquefaciens* deposited in the Spanish Type Culture Collection (CECT) with the access number CECT8836, or a mutant thereof, wherein said mutant: (a) is obtained using the strain CECT8836 of *Bacillus amyloliquefaciens* as starting material, and (b) maintains antagonistic activity as well as the ability to colonise or survive from the starting strain in a part of a plant.

The strain of *Bacillus amyloliquefaciens* of the invention, isolated from *Lobularia maritima* flowers from the region of Girona, was deposited by the applicant, according to the Budapest Treaty, on Feb. 11, 2015 in the Spanish Type Culture Collection (CECT), located at the University of Valencia, Edificio de investigación, Campus de Burjassot, 46100 Burjassot, Valencia, Spain. The strain was given the access number CECT8836 after it was considered viable.

The invention also relates to mutants of the strain CECT8836 of *Bacillus amyloliquefaciens*. By the term "mutants" is understood bacteria that are obtained using, as starting material, the strain CECT8836 of *B. amyloliquefaciens* of the invention, and that are characterised in maintaining the properties of said deposited strain, concerning their antagonistic capacity against phytopathogenic bacteria, biosafety and ecological aptitude for colonising plants. A "mutant" of CECT8836 of *B. amyloliquefaciens* is also understood according to the invention as a "variant" of CECT8836 of *B. amyloliquefaciens*. The skilled in the art will understand that mutants retaining the characteristics and relevant advantages described herein can be obtained routinely, for example by spontaneous mutagenesis or directed mutation, using the strain of the invention as starting material. Methods for obtaining mutants of a specific bacterial strain are known in the art. An example can be found in Sambrook, J. and Russell, D. W. "Molecular Cloning: A Laboratory Manual", Chapter 13, "Mutagenesis", Cold Spring Harbor, 3rd Ed, 2001.

In the present invention the term "strain of the invention" refers not only to the strain CECT8836 of *B. amyloliquefaciens*, but also to mutants thereof.

As illustrated below, the strain of the invention is characterised by showing:
(i) antagonistic activity of the starting strain against bacteria *Erwinia amylovora*, *Pseudomonas syringae* pv *syringae*, *P. syringae* pv *tomato*, *Xanthomonas axonopodis* pv *vesicatoria*, *X. arboricola* pv *fragariae*, *Clavibacter michiganensis* subsp. *michiganensis*, *Ralstonia solanacearum*, *Rhizobium radiobacter*, *Pectobacterium carotovorum*, and against the fungi *Phytophthora cinnamomi*, *P. cactorum*, *Penicillium expansum*, *Botrytis cinerea*, *Fusarium oxysporum* and *Pytium ultimum* (FIG. 3);
(ii) presence of the genes fenD, srfAA, bacA, spaS, bmyB, and ituC related to the synthesis of antimicrobial peptides (FIG. 1). Furthermore, it was found that this strain also included the genes beaS, dfnM, dhbA and mlnI, related to the synthesis of polyketides and other various compounds with antimicrobial activity;
(iii) ability to colonise and survive in an aerial part of a plant; and
(iv) ability to inhibit infections caused by *E. amylovora* and *P. syringae* pv. *syringae* in pear trees, by *P. syringae* pv. *tomato* in tomato plants; and by *X. axonopodis* pv. *vesicatoria* in pepper plants (FIG. 6).

The high antagonistic activity of the strain of the invention is partly due to the production of peptide and non-peptide compounds, which inhibit the growth of pathogenic bacteria and fungi. Among these compounds, the surfactins, fengycins, bacillomycins, iturins, bacilysin and subtilisin stand out. Although many *Bacillus* strains contain genes related to the biosynthesis of these peptides with antimicrobial activity, not all of these strains show antagonistic activity against plant pathogens, either bacterial or fungal. In this regard, Example 1 below shows that many *Bacillus* strains (having genes for the synthesis of any of these antimicrobial peptides), have no remarkable antagonistic activity against phytopathogenic fungi and bacteria. However, in FIG. 3 can be seen that the strain CECT8836 of *B. amyloliquefaciens* of the invention exhibits a broad spectrum of prominent antagonism against various bacterial phytopathogens, as well as against various phytopathogenic fungi. Said surprising antagonistic effect is also reflected in FIG. 6, wherein the effectiveness of the strain of the invention in inhibiting infections of *E. amylovora*, *P. syringae* pv. *syringae* in pear trees, *P. syringae* pv *tomato* in tomato plants and *X. axonopodis* pv *vesicatoria* in pepper plants, is shown. In Example 1 is also shown that the strain of the invention has the ability to produce all the detectable isoforms from the different antimicrobial peptides analysed (FIG. 2) where the surfactins, fengycins, bacillomycins and iturins are included. Furthermore, surprisingly, as already indicated above, the strain CECT8836 has 6 genes related to the synthesis of antimicrobial peptides, and 4 other genes related to the synthesis of polyketides and other various compounds with antimicrobial activity. This antimicrobial profile, that is, large number of genes involved in the synthesis of different antimicrobials for a wide range of activities, is something peculiar and surprising of the strain of the invention when compared to other strains of *Bacillus* from natural environments related to plants (see FIG. 1, where other *Bacillus* strains isolated from the environment are listed).

In the present invention, the term "ecological aptitude" refers to the ability of a micro-organism to colonise, multiply in favourable conditions, and survive in adverse conditions in an environment (in this case a plant).

In the present invention the term "aerial part of a plant" includes the flower, leaf and fruit of a plant.

The plant may be a vegetable plant or fruit tree type, such as a pear tree, tomato, cauliflower or pepper, among others.

The presence of genes related to the synthesis of antimicrobial peptides may be determined by PCR analysis using primer pairs defined by the sequences SEQ ID NO: 3-26 as disclosed in Example 1. Antagonistic activity in vitro and ex vivo against phytopathogenic fungi and bacteria can be determined as disclosed in Examples 3-4. The ability to inhibit infections caused by *E. amylovora*, *P. syringae* pv *syringae*, *P. syringae* pv *tomato* and *X. axonopodis* pv *vesicatoria* can be determined as disclosed in Example 3. The ability to colonise and survive in plants under field conditions is described in Example 6. The ability to control fungal and bacterial diseases under field conditions can be determined as disclosed in Example 7.

The strain of the invention has several advantages that make it particularly suitable for use in integrated pest control. In the present invention, the term "integrated pest control" (or "integrated pest management") has the usual meaning in the field of agriculture, where it is understood as a strategy that uses a variety of complementary methods: physical, mechanical chemical, biological, genetic, legal and cultural, for the control of pests. These methods are applied in three stages: prevention, observation and application. It is an ecological approach that aims to reduce or eliminate the use of synthetic chemical pesticides and minimise the impact on the environment. It can also be referred as ecological and biological pest control. Thus, the terms "pest control", and "biological pest control" are used herein interchangeably and refer to integrated pest control.

On one hand, members of the species *B. amyloliquefaciens* in particular, are safe being considered as GRAS by the FDA in the United States and as QPS by EFSA in the European Union. Accordingly, the strain of the invention is suitable for use in agriculture.

In addition to its recognised biosafety, as shown below, the strain of the invention is highly effective in preventing infections caused by different bacterial and fungal pathogens in vegetable plants and fruit trees. From the data shown below it can also be concluded that this effectiveness is mainly due to its high antagonistic activity against these pathogens and its surprising ecological aptitude to colonise and survive in the aerial organs of plants such as leaves, fruits and/or flowers. In particular, Example 6 shows that the strain of the invention has a great ability to colonise and survive in the organs of the plants to be protected against different infections, especially bacterial diseases. This surprising ecological aptitude is very important for the biological control of pests.

In view of the above, in another aspect, the invention refers to the use of the strain CECT8836 of *B. amyloliquefaciens* or a mutant thereof, as a pesticide in plants.

In the present invention, the term "pesticide" is understood by its usual meaning in the field of agronomy as a product intended to kill, repel, regulate or disrupt the growth of living organisms that are considered pests. Clearly, due to the nature of the strain CECT8836 of *B. amyloliquefaciens* or mutant thereof, herein it is understood that "pesticide" is a biological or ecological pesticide, also called biopesticide. In the scope of the present invention, the term "pesticide" would have the same meaning as the term "phytosanitary".

In a further aspect, the invention provides the use of the strain CECT8836 of *B. amyloliquefaciens* or a mutant thereof to control a disease caused by a bacterium or fungus in a plant.

In the present invention, the term "control of the disease" means that it prevents, cures or eradicates the disease.

In one embodiment, the plant to be treated is a vegetable plant or fruit tree.

In another embodiment, the strain of the invention or a mutant thereof is used in preventing infections caused by bacteria or fungi in plants.

With regard to its use as a pesticide in plants, it is important to obtain large quantities of viable cells of the strain. As shown in Example 5, once concentrated and lyophilised, the composition shows 100% cell viability, which is maintained during storage.

In another aspect, the present invention relates to a method for obtaining a suspension of viable cells derived from the strain of the invention comprising: (i) inoculating the strain of the invention in a suitable culture medium, and (ii) subjecting the inoculated culture medium of step (i) to appropriate conditions to the growth of the strain.

The term "derived from the strain of the invention" means that the suspension is obtained from the strain object of the present invention.

The strain of the invention may be inoculated in the culture medium at a final concentration comprised from 1 to 5%. Preferably the inoculated culture is in an exponential growth phase. Cell growth will slow on achieving, preferably, a cell concentration comprised from $7 \times 10^{*8}$ to $2 \times 10^{*9}$ CFU/mL. Suitable culture media for the growth of the strain of the invention are synthetic media, such as LB (lysogenic broth) and PM (saline production medium), or media of plant origin such as molasses (e.g. from sugar cane, beets). Suitable conditions for strain's growth are temperatures comprised from 25 to 35° C., pH comprised 6 to 8, and oxygen concentration comprised from 10 to 50%. The growth of the strain of the invention is produced by stirring. An example of the detailed method for obtaining cells from the strain of the invention is reflected in Example 4.

In another embodiment of the method for obtaining the suspension, cells are separated from the medium to obtain a concentrated suspension. Suitable separation techniques include centrifugation or filtration of the culture. Carrying out the centrifugation of the culture, for example, at a minimum of 8000 rpm, cells are obtained in the pellet, which are resuspended in part of the culture medium or in a suitable buffered medium such that the strain concentration is approximately about $10^{10}$ CFU/mL.

Once the suspension is obtained, it may be subjected to a dehydration step. Dehydration can be carried out through a lyophilisation process. Alternatively, the suspension can be dehydrated by fluidised bed drying. Another option is to dehydrate the suspension by spray drying. In this regard, another advantageous feature of the strain of the invention is that it exhibits high resistance to dehydrating processes, which are routine in obtaining microorganisms on an industrial scale. In order to improve cell viability, an inert osmotic protector ingredient can be added to the suspension before carrying out the dehydration process.

In another particular embodiment, the method for obtaining the viable cell suspension of the invention comprises resuspending the cells resulting from the separation step in a suitable buffer to yield a cell concentrated suspension.

With a view to practical use in pest control, pesticide agents are usually formulated into compositions also including suitable additives for agricultural use. The compositions of the invention may be solid (including, for example, dehydrated bacteria concentrate) or liquid (including bacteria concentrated suspensions).

"Suitable compounds for agricultural use" refers to those compounds and/or materials which are suitable for use in agriculture. In general, said compounds should be non-toxic to humans and preferably should be environment-friendly.

In a particular embodiment, the pesticidal compositions of the invention may contain compounds for improving the adhesion of the strains in the plants to be treated, such as phytostrengthener compounds, nutrients, wetting agents, stabilisers, osmotic protectors, antioxidants, sunscreens, buffering compounds or combinations thereof. Some compounds for improving adhesion are gelatin, starch, pectins, alginates and various types of gums such as xanthan. Many of these compounds are also wetting agents. Congo red is included among the sunscreens dyes. The phytostrengtheners are compounds that can facilitate make crops develop robustness or tolerance towards pathogens or adverse environmental conditions, for example, jasmonic acid analogues and some plant defence stimulants such as harpins, chitosans, and laminarins. In particular the pesticidal compositions of the invention contain at least one osmotic protector as an additive. Examples of osmotic protector compounds are betaines, amino acids and trehalose.

In a further aspect the present invention provides a composition that comprises the strain of the invention and at least one additional pesticidal agent, said additional pesticide not adversely affecting the activity of the strain CECT8836. In one embodiment, the composition of the invention comprises an additional pesticide. In another embodiment, the additional pesticidal agent is selected from the group consisting of a bacterial strain effective in controlling a bacterial or fungal infection, a fungicide, an insecticide or a nematicide.

In one particular embodiment, the additional pesticidal agent is another bacterial strain effective in controlling bacterial or fungal infection. Among the bacterial strains effective in controlling various infections, besides the CECT8836 strain of the invention, there is another strain of *B. amyloliquefaciens*, the CECT8837, or a mutant thereof, isolated by the inventors of the present invention. In one embodiment, the composition of the invention comprises CECT8836 of *B. amyloliquefaciens* and CECT8837 of *B. amyloliquefaciens* together with suitable additives for agricultural use.

In another aspect, the invention refers to a strain of *Bacillus amyloliquefaciens* deposited in the Spanish Type Culture Collection (CECT) with the access number CECT8837, or a mutant thereof, wherein said mutant: (a) is obtained using the strain CECT8837 of *Bacillus amyloliquefaciens* as starting material, and (b) is characterised by maintaining antagonistic activity and the ability to colonise and survive from the starting strain in an aerial part of a plant.

The strain CECT8837 of *B. amyloliquefaciens*, isolated from leaves of a silver fir from the region of Lleida (Spain), was deposited by the applicant, according to the Budapest Treaty, on 11 Feb. 2015 in the Spanish Type Culture Collection (CECT), located at the University of Valencia, Edificio de investigación, Campus de Burjassot, 46100 Burjassot, Valencia, Spain. The strain of *B. amyloliquefaciens* was given the access number CECT8837.

"Mutant" is understood as being a bacterium that is obtained using the strain CECT8837 of *B. amyloliquefaciens* of the invention as starting material, and which is characterised by maintaining the properties of the deposited strain, with regard to the antagonistic capacity against phytopathogenic bacteria, biosafety and ecological aptitude in colonising plants. A "mutant" of CECT8837 of *B. amyloliquefaciens* is also understood, according to the invention, as a "variant" of CECT8837 of *B. amyloliquefaciens*. The skilled in the art will understand that mutants retaining the features and relevant advantages described herein can be obtained routinely using this strain of the invention as starting material—for example by spontaneous mutagenesis or directed mutation. Methods for obtaining mutants of a specific bacterial strain are known in the art. An example can be found in Sambrook, J. et al., 2001 cited above.

Similarly with the strain CECT8836 of *B. amyloliquefaciens*, the inventors have observed that the strain CECT8837 of *B. amyloliquefaciens* and mutants thereof have advantageous properties for use as pesticide in controlling fungal or bacterial infections in plants, especially those caused by bacteria. This strain is safe, it has high antagonistic activity against a wide variety of bacterial and fungal pathogens and it is able to colonise and survive in plants under different environmental conditions. As illustrated in the examples below, the strain CECT8837 is characterised by the following properties:

(i) antagonistic activity against the bacteria *Erwinia amylovora*, *Pseudomonas syringae* pv *syringae*, *P. syringae* pv *tomato*, *Xanthomonas axonopodis* pv *vesicatoria*, *X. arboricola* pv *fragariae*, *Clavibacter michiganensis* subsp. *michiganensis*, *Ralstonia solanacearum*, *Agrobacterium tumefaciens*, *E. carotorova*, and against fungi *Phytophthora cinnamomi*, *P. cactorum*, *Penicillium expansum*, *Stemphylium vesicarium*, *Botrytis cinerea* and *Pytium ultimum*; and does not have any antagonism against *F. oxysporum*;

(ii) presence of genes fenD, srfAA, bacA, bmyB, and ituC, related to the synthesis of antimicrobial peptides (FIG. 1). Furthermore, it was found that this strain also included genes beaS, dfnM, dhbA and mlnI, related to the synthesis of polyketides and other various compounds with antimicrobial activity. This strain, unlike the strain CECT8836, does not have the genes spaS;

(iii) the ability to colonise and survive in an aerial part of the plant; and (iv) the ability to inhibit infections caused by *E. amylovora* and *P. syringae* pv. *syringae* in pear trees, by *P. syringae* pv. *tomato* in tomato plants; and by *X. axonopodis* pv. *vesicatoria* in pepper plants.

Thus, the present invention refers to the use of the strain CECT8837 as a pesticide in a plant, particularly in the prevention, treatment or eradication of diseases caused by bacteria or fungi in plants, preferably of the vegetable or fruit tree type. Other aspects refer to compositions comprising the strain or a mutant thereof with agriculturally acceptable compounds and/or at least one pesticide, said compounds not adversely affecting the activity of the strain CECT8837 and said pesticides being as defined above; and the use of said compositions in controlling infection in plants caused by bacteria or fungi.

The invention also relates to a method for obtaining a suspension of viable cells from CECT8837 of *B. amyloliquefaciens* or a mutant thereof, which is analogous to that described for CECT8836 of *B. amyloliquefaciens*.

The invention relates, in another aspect, to a cell-free extract derived from the strain CECT8836 of *B. amyloliquefaciens*, CECT8837 of *B. amyloliquefaciens*, or a mutant thereof, obtainable by a process comprising: (i) inoculating the strain of the invention in a suitable culture medium, (ii) subjecting the inoculated culture medium to suitable growth conditions, (iii) separating the cells from the culture medium of step (ii), (iv) collecting the cell-free extract; and (v) optionally subjecting the cell-free extract to a concentration process.

Culture media, inoculation conditions and growth conditions suitable for the strain of the invention for obtaining the extract are the same as those described above for the process for obtaining a cell suspension from the strain CECT8836 or a mutant thereof. Preferably, the cell growth will slow in a steady phase, more preferably after 30-48 hours. In another embodiment, step (ii) takes place at a temperature comprised from to 35° C., a pH comprised from 6 to 9, and an oxygen concentration comprised from to 50%, with stirring until achieving a cell concentration higher than $1 \times 10^{*}9$ CFU/mL. As for stage (v) non-limiting examples of suitable concentration processes are dehydration (lyophilisation, spray drying), filtration, ultra-filtration, precipitation, centrifugation, and chromatography. Additionally, in order to increase their activity, the extract of the invention can be subjected to a fractionation process to separate the most active fractions. Preferably, the fractionation comprises a molecular discrimination chromatography and/or reverse phase.

The extracts of the strains CECT8836 and CECT8837 of *B. amyloliquefaciens* or a mutant thereof can be directly used in the control of bacterial and fungal diseases, but preferably, will be part of a pesticidal composition with other agriculturally acceptable compounds. Therefore, further aspects of the invention provide a composition that comprises the extract of the invention, one or more agriculturally acceptable compounds and/or one or more additional pesticides, as well as the use of said compositions as a pesticide and in the control of diseases caused by bacteria or fungi in plants. In one embodiment, the pesticidal composition comprises a cell-free extract obtained from CECT8836, as defined above, and an additional pesticide selected between the strain CECT8836 and the strain CECT8837. In another embodiment, the pesticidal composition comprises a cell-free extract obtained from the strain CECT8837 and an additional pesticide selected between the strain CECT8836 and the strain CECT8837.

Finally the invention relates to a method for biological controlling of a bacterial or fungal disease in a plant that comprises administering a strain of the invention (CECT8836, CECT8837) or mutant thereof, a composition, a suspension comprising said strain, or a cell-free extract derived from said strain.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

Example 1. Isolation and Characterisation of the Strains CECT8836 of *B. amyloliquefaciens* and CECT8837 of *B. amyloliquefaciens*

Figure 1:
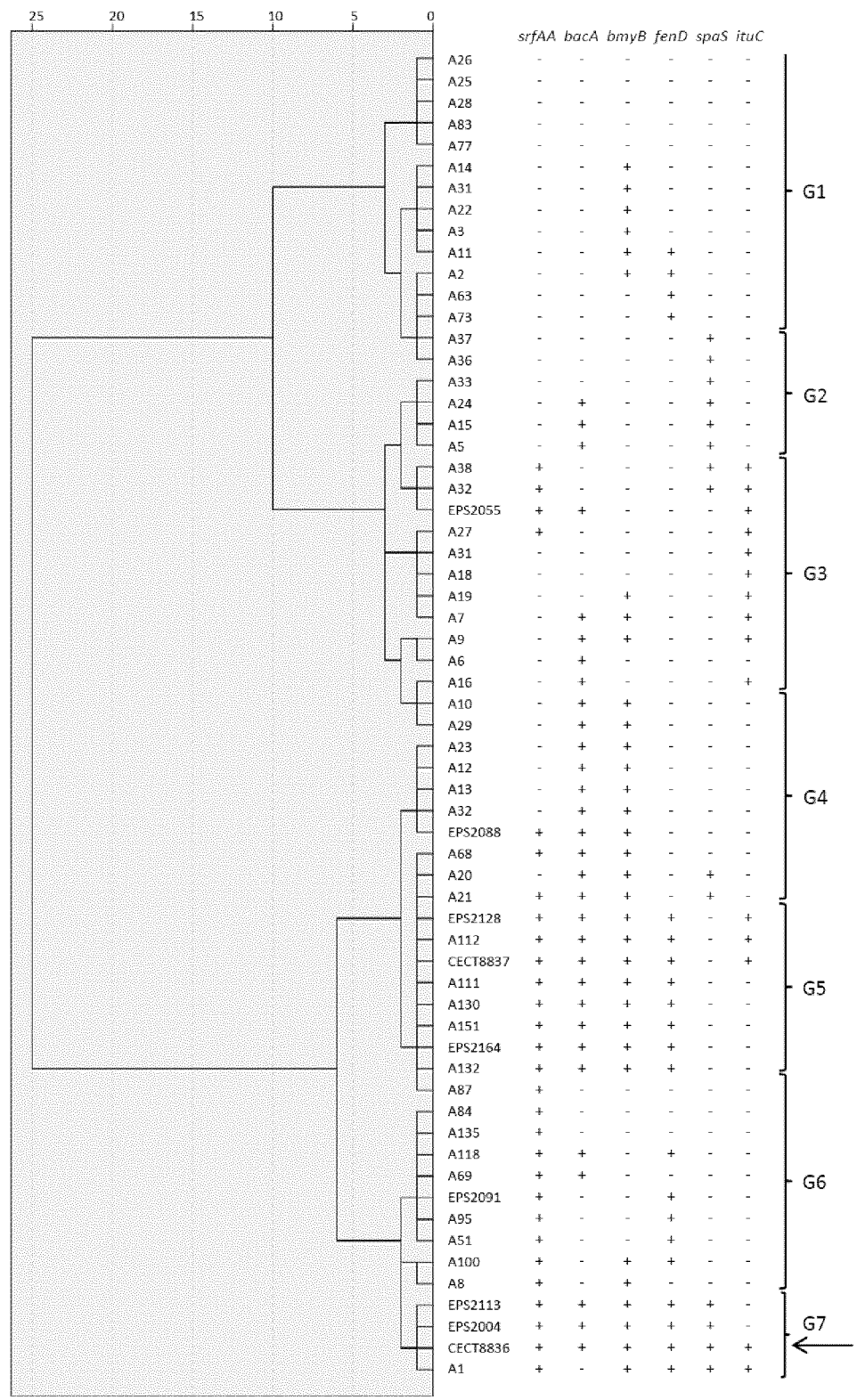
FIG. 1. Dendrogram corresponding to the dissimilarity coefficient of 64 isolates from *Bacillus* sp. as a function of their profile of presence of biosynthetic genes from antimicrobial peptides (srfAA, bacA, bmyB, fenD, spaS and ituC). Symbols indicate the presence (+) or absence (−) of the gene. Seven major clusters with a 7-level dissimilarity (G1, G2, G3, G4, G5, G6, G7) as well as the position of the strain CECT8836 in the dendrogram (arrow) are indicated.

In order to obtain the isolates, samples of leaves, flowers and fruits collected from commercial fields of vegetable plants and pome fruit trees were taken, as well as wild plants in lands adjacent to commercial plots. All samples were from fields and natural environments of Mediterranean climate. The samples were processed by conventional microbiological methods (Mora et al., "Antimicrobial peptide genes in *Bacillus* strains from plant environments", International Microbiology, 2011, vol. 14, pp. 213-223), and bacteria of the genus *Bacillus* were isolated in LB medium at 40° C. for 48 h, forming a collection of 68 isolates. Said isolates were subjected to a study to determine the presence of genes srfAA, bmyB, ituC, fenD, spaS and bacA, involved in the production of antimicrobial peptides (AMPs), namely, of the cyclo-lipopeptides surfactin, bacilomicin, iturin and fengycin, the lantibiotic subtilin, and the dipeptide bacilysin, respectively (Chen et al., "Comparative analysis of the complete genome sequence of the plant growth-promoting bacterium *Bacillus amyloliquefaciens* FZB42", Nature Biotechnology, 2007, vol. 25, pp. 1007-1014). The DNA of the isolates and of the reference strains FZB42 of *B. amyloliquefaciens* (positive control) (Koumoutsi et al., Structural and Functional Characterization of Gene Clusters Directing Nonribosomal Synthesis of Bioactive Cyclic Lipopeptides in *Bacillus amyloliquefaciens* Strain FZB42, 2004, Journal of Bacteriology, vol. 186, pp. 1084-1096) and *B. polymyxa* RGAF84 (negative control) (Landa et al., Integrated management of *Fusarium* wilt of chickpea with sowing date, host resistance, and biological control, 2004, Phytopathology, Vol. 94, pp. 946-960) were used to verify the correct amplification of genes through PCR. The DNA was obtained from cultures of the strain in exponential phase obtained, culturing in LB broth inoculated at 1% (vol/vol) and incubated at 28° C. with stirring (100 rpm). The material obtained was subjected to centrifugation at 8000 rpm for 15 minutes and the pellet containing cells and spores was used to extract the DNA using Tris-saline-EDTA-SDS antioxidant and isopropanol precipitation, adjusting the concentration to 10 ng DNA/µL using the Nanodrop system. Amplification reactions were performed under standard conditions using the primers defined for each of the genes. Specifically, the sequences SEQ ID NO: 1 (srfAAF: TCGGGACAG-GAAGACATCAT) y 2 (srfAAR: CCACTCAAACGGA-TAATCCTGA) for srfAA gene, SEQ ID NO: 3 (bmyBF: GAATCCCGTTGTTCTCCAAA) and 4 (bmyBR: GCGGGTATTGAATGCTTGTT) for bmyB gene, SEQ ID NO: 5 (ituCF: GGCTGCTGCAGATGCTTTAT) and 6 (ituCR: TCGCAGATAATCGCAGTGAG) for ituC gene, SEQ ID NO: 7 (fenDF: GGCCCGTTCTCTAAATCCAT) and 8 (fenDR: GTCATGCTGACGAGAGCAAA) for fenD gene, SEQ ID NO: 9 (spaSF: GGTTTGTTGGATG-GAGCTGT) and 10 (spaSR: GCAAGGAGTCAGAG-CAAGGT) for spaS gene, and SEQ ID NO: 11 (bacAF: CAGCTCATGGGAATGCTTTT) and 12 (bacAR: CTCG-GTCCTGAAGGGACAAG) for bacA gene. The conditions were of 4 min at 95° C., 35 cycles of 1 min at 94° C., 1 min at 58° C., and 1 min at 72° C., with a step of final extension of 5 min at 72° C. followed by a stop at 4° C. For the primers of bmyB gene, the annealing temperature was 55° C. instead of 58° C. The amplified products were separated by electrophoresis in agarose gel at 1.8% in 1× Tris-acetate-EDTA (TAE) for 45 min at 90 V and visualized with ethidium bromide. Surprisingly, there was great diversity in terms of the presence of the genes. Among the isolates it was observed that the distribution of these genes was quite scattered, but that the presence of more than 3 genes simultaneously was less frequent (FIG. 1). The strains were distributed into 7 groups. The strain CECT8836 appears in group 7. This strain stands out because it is the only one which comprises all the genes amplified. The strain CECT8837 appears in group 5 and is characterised by having genes srfAA, bacA, bmyB, ituC and fenD, but does not have the gene spaS. In addition to these genes, in strains CECT8836 and CECT8837 also the genes beaS, mlnI, dfnM and dhbA related to the synthesis of bacillaene polyketides, macrolactin and dificidin, as well as the siderophore bacillibactin, respectively, were detected. These genes are detected with the sequences SEQ ID NO: 19 (beaSF1: CGCAAAAGCTCTTCGACCGCCGTC) and (beaSR1: CTCTCGTGCCGTCGGAATATCCGC) for beaS gene, SEQ ID NO: 21 (dfnMF1: CGGAGTGAAACCGTGC-CGGGATAAAGA) and 22 (dfnMR1: GACCATTCA-GAGCGGAAAGCTCC) for dfnM gene, SEQ ID NO: 23 (mlnIF1: GGAAGAAAAACAGTCGAGGCGATGCTG) and 24 (mln1R1: GAGAAGCTCCGCCGTCACCAGTG) for mlnI gene, SEQ ID NO: 25 (dhbAF1: CGCCTAAAG-TAGCGCCGCCATCAACGC) and 26 (dhbAR2: CCGC-GATGGAGCGGGATTATCCG) for dhbA gene (Arguelles-Arias et al., *Bacillus amyloliquefaciens* GA1 as a source of potent antibiotics and other secondary metabolites for biocontrol of plant pathogens. 2009. *Microbial Cell Factories*. Vol: 8, Art: 63).

The cyclo-lipopeptide production pattern (including fengicins, iturins, surfactins) of the 68 isolates obtained from *Bacillus* was also determined. First, cyclo-lipopeptide extraction was performed from the culture of the strains in LB medium for 48 h at 28° C. by mixing the cell-free culture supernatant with isoamyl alcohol in equal proportion. The mixtures were stirred vigorously for 2 minutes and then the organic phase (upper phase) was recovered by centrifuging the mixture for 10 minutes at 10,000 rpm. Subsequently, the organic phase was evaporated by using an evaporator (Scan Speed Teflon, AAPPTEC, LCC, Louisville, USA) and dissolved in distilled water containing 0.085% trifluoroacetic acid (TFA). The already dissolved organic phase was fractionated by high pressure liquid chromatography (HPLC) using the Agilent Technologies 1200 Series instrument and using a Kinetex XB-C18 reverse phase column (Phenomenex, Madrid, Spain). Elution was carried out under the following conditions: linear gradient of 2-50% acetonitrile containing 0.085% TFA for 18 min, linear gradient of 50-100% acetonitrile for 4 minutes at a constant flow rate of 1.85 ml/min. The eluted compounds were detected by absorbance at 220 nm.

Figure 2:
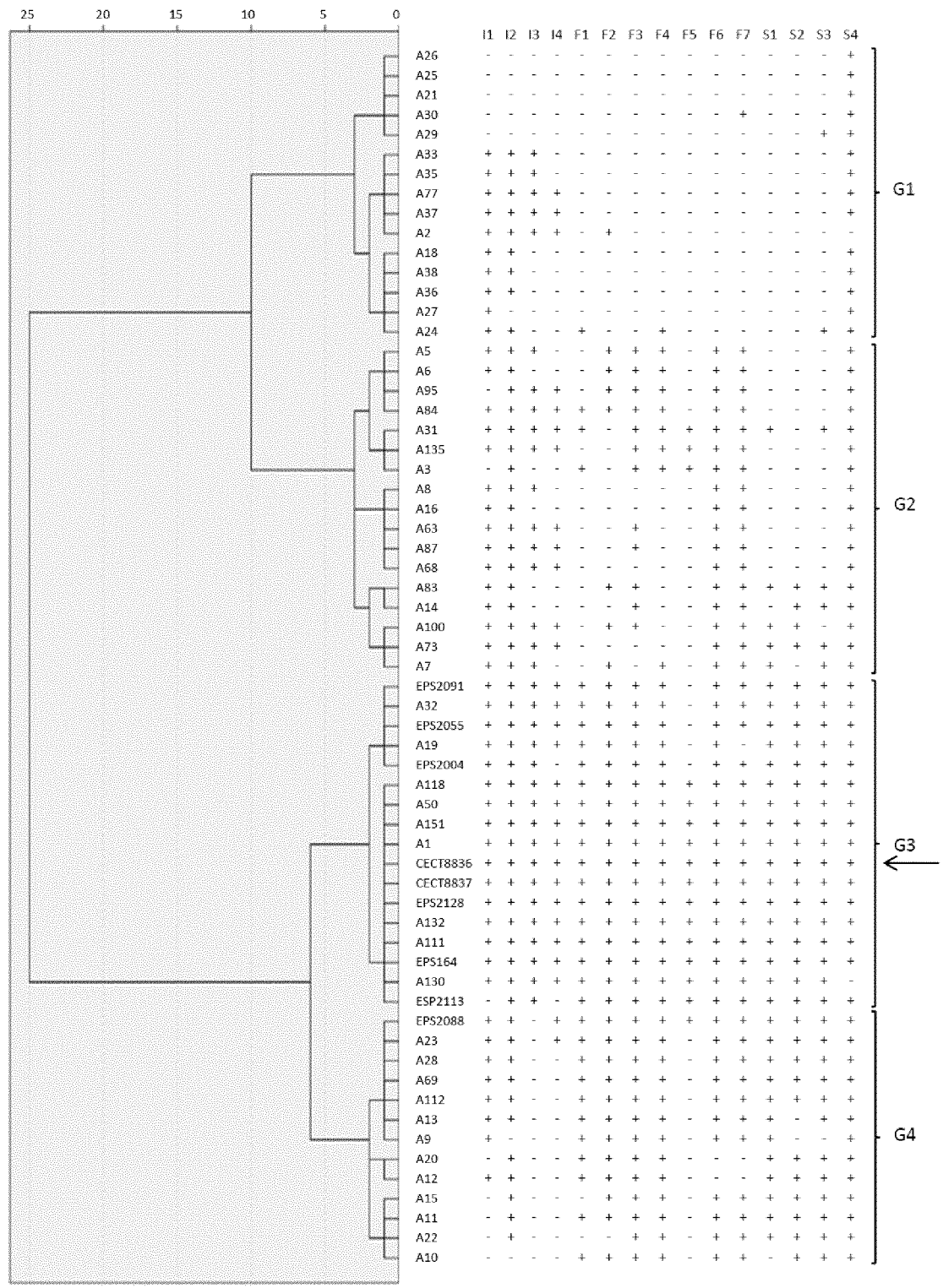
FIG. 2. Dendrogram corresponding to the dissimilarity coefficient of 64 isolates from 10 *Bacillus* sp., as a function of their profile of production of isoforms of cyclic peptides corresponding to the families of the iturins (11, 12, 13, 14), fengycins (F1, F2, F3, F4, F5, F6, F7) and surfactins (S1, S2, S3, S4). Symbols indicate the presence (+) and absence (−) of the major isoform. Four major clusters with a 5-level dissimilarity (G1, G2, G3, G4) and the position of the strains CECT8836 in the dendrogram (arrow) are indicated.

The fractions obtained were analysed by using two techniques of mass spectrometry, specifically, they were analysed through MALDI-TOF by using the Bruker Daltonics Ultraflex instrument (Bruker Daltonics, Bruker Corporation, Billerica, USA) and also through ESI-MS by using the Esquire 6000 ESI ion Trap LC/MS instrument (Bruker Daltonics, Bruker Corporation, Billerica, USA). By using these two techniques in parallel it was possible to assign each elution peak to each cyclo-lipopeptide based on their molecular mass. Production results for the 68 strains were analysed through a hierarchical analysis by using the squared Euclidean distance using the PC-SAS software (version 9.1; SAS Institute Inc., Cary, N.C.) (FIG. 2). The strains were distributed into 4 groups characterised by the differential production of the different isoforms. The strains CECT8836 and CECT8837 of B. amyloliquefaciens were clustered into group 3. This group is characterised by grouping productive strains of most of the isoforms corresponding to the three cyclo-lipopeptide families analysed, namely the fengycins, iturins, surfactins. It was surprisingly found that strains CECT8836 and CECT8837 produced all the 15 isoforms of CLPs.

Figure 3:
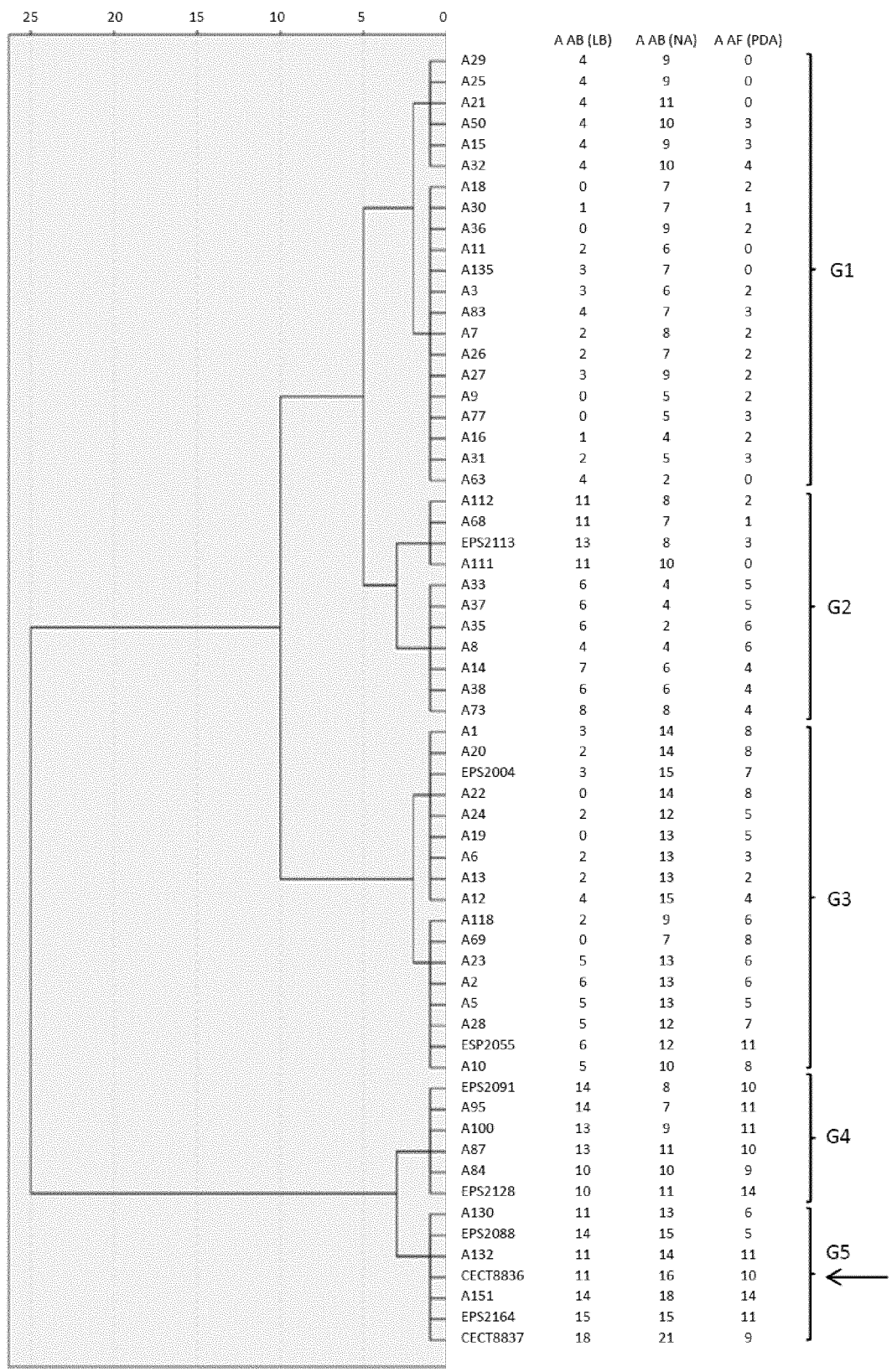
FIG. 3. Dendrogram corresponding to the dissimilarity coefficient of 64 isolates from *Bacillus* sp., as a function of their profile of in vitro antagonism in LB and NA agar, against eight phytopathogenic bacteria (*Erwinia amylovora* PMV6076, *Pseudomonas syringae* pv *syringae* EPS94, *P. syringae* pv *tomato* DC3000, *Xanthomonas axonopodis* pv *vesicatoria* CFBP3275, *X. arboricola* pv. *fragariae* CFBP3549, *Clavibacter michiganensis* subsp. *michiganensis* CECT790, *Ralstonia solanacearum* CECT125, *Rhizobium radiobacter* CECT472 and *Pectobacterium carotovorum* CECT225), and in PDA, against five phytopathogen fungi (*Phytophthora cinnamomi* CECT2965, *P. cactorum* F490, *Penicillium expansum* EPS26, *Fusarium oxysporum* ATCC201829 and *Pythium ultimum* CECT2364). The inhibitory activity of each *Bacillus* strain against each indicator was classified into: 1, halus of inhibition smaller than 10 mm; 2, halus of inhibition between 10 and 20 mm; 3, halus of inhibition greater than 20 mm. Finally, a global activity index (GAI) for each *Bacillus* strain was calculated from the summ of the inhibitory activity for the corresponding fungi or bacteria indicators and culture medium used. GAI maximum values were 24 for activity against bacteria (8 indicator bacteria for a maximum activity level of 3) and 15 for activity against fungi (5 indicator fungi for a maximum activity level of 3). Thus, higher values indicate a high antifungal/antibacterial activity, with a broad spectrum of activity. With the inhibitory activity data of each strain the matrix for the distances between different strains is calculated by the Ward's method and the dendrogram of the figure is finally obtained. This method allows for calculating the dissimilarity coefficient between two strains so that the respective distance is greater the higher its value is (the strains are more different). Five major clusters with a 3.5-level dissimilarity observed (G1, G2, G3, G4, G5) and the position of the strain CECT8836 in the dendrogram (arrow) are indicated.

The 68 strains of Bacillus spp. were also in vitro tested for antimicrobial activity against eight phytopathogen bacteria (Erwinia amylovora PMV6076, Pseudomonas syringae pv syringae EPS94, P. syringae pv tomato DC3000, Xanthomonas axonopodis pv vesicatoria CFBP3275, X. arboricola pv. fragariae CFBP3549, Clavibacter michiganensis subsp. michiganensis CECT790, Ralstonia solanacearum CECT125, Rhizobium radiobacter CECT472 and Pectobacterium carotovorum CECT225) and 5 phytopathogen fungi (Phytophthora cinnamomi CECT2965, P. cactorum F490, Penicillium expansum EPS26, Fusarium oxysporum ATCC201829 and Pytium ultimum CECT2364), by using the technique of colony replication in overlayer of Luria Bertani (LB) agar and nutrient agar (NA) for bacteria and overlayer of potato dextrose agar (PDA) for fungi. The growth inhibition halos for the indicators were determined after 48 h at 28° C. for bacteria and after 4 days at 25° C. for fungi. The inhibition diameter results were normalised and used to perform a hierarchical clustering analysis by using the Jaccard dissimilarity coefficient with the UPGMA algorithm (NTSYS, Exeter, USA) (FIG. 3). 5 different clusters are observed as a function of the pattern of antibacterial and antifungal activity with a similarity level of 5, with the G5 group including the most active strains, both in terms of level of activity and spectrum of activity against phytopathogen bacteria and fungi. Again and unexpectedly, this group includes the strains CECT8836 and CECT8837. The remaining groups presented strains with lower activity or limited spectrum of activity to some pathogens or to a culture medium. Therefore, the strains CECT8836 and CECT8837 have a powerful antifungal and antibacterial effect of broad spectrum, which differentiate them from the rest of the isolates obtained from natural sources.

In order to determine the Bacillus species to which the 15 isolates having an increased presence of biosynthetic genes from AMPs and increased antimicrobial activity and spectrum, a biochemical characterisation using an API® 50 CHB/E strip (Biomerieux, France) was performed. From the pure cultures grown at 28° C. for 24 hours, a suspension was obtained of which 200 µl were plated into each well after mixing with E medium. The test strips were read after incubation at 37° C. for 16-24 h depending on each strain. A positive test appeared as red due to the shift of the colorimetric indicator as a consequence of the medium acidification. The program API system databases APILAB Plus software version 3.3.3 (BioMemrieux, France) was used to determine the strain. The strains QST713 and FZB42 of Bacillus amyloliquefaciens and the strains UMAF6614 and UMAF6639 of B. subtilis were included as reference controls. Thus, it was concluded that the strains CECT8836 and CECT8837 of B. amyloliquefaciens were B. subtilis/B. amyloliquefaciens and were closely related to the reference strains.

Figure 4:
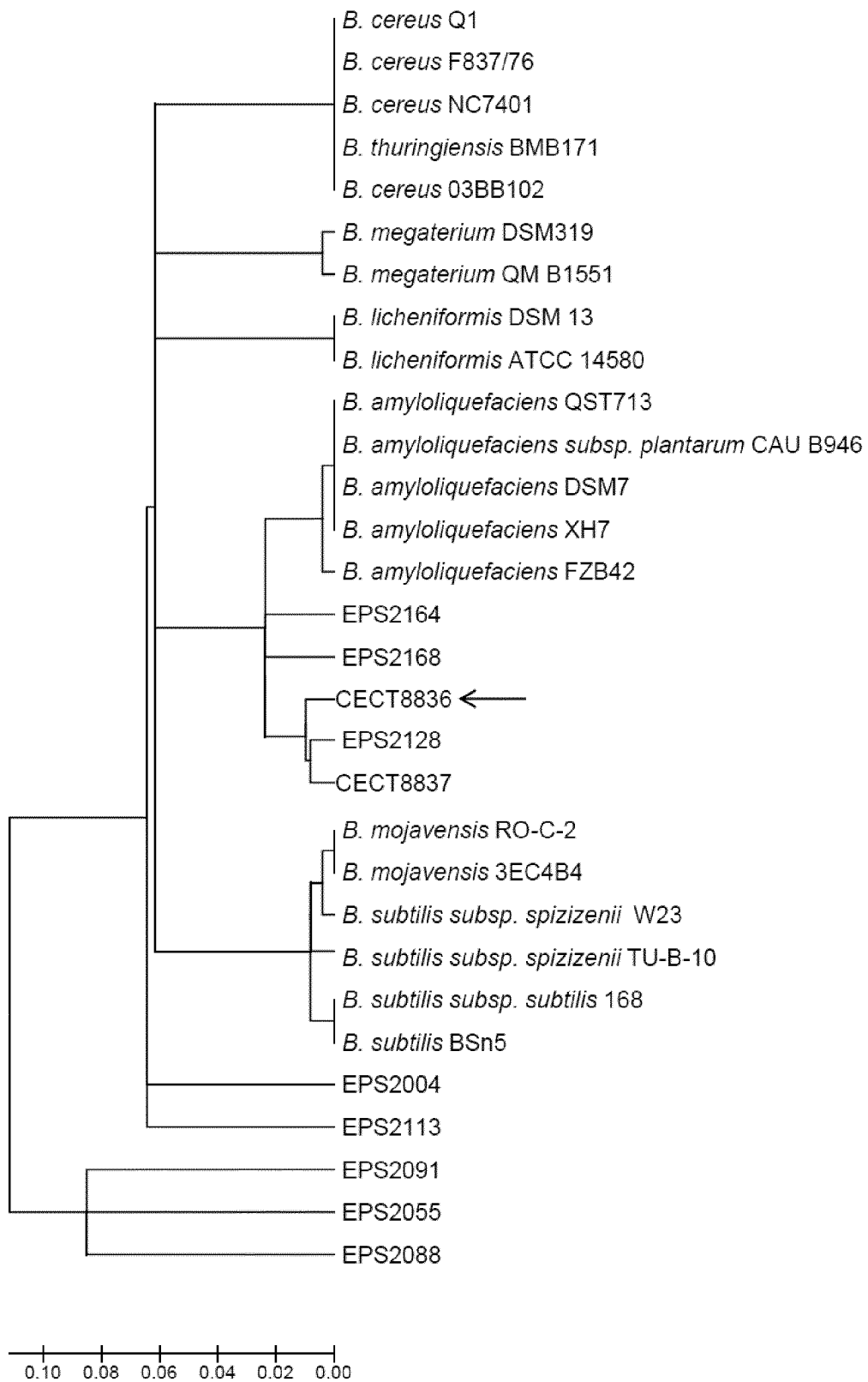
FIG. 4. Phylogenetic tree corresponding to the dissimilarity coefficient for 31 strains of *Bacillus* sp., as a function of the interrelationship between the rpoB gene sequences of the different strains. The position of the strain CECT8836 is indicated in the dendrogram (arrow).

In order to identify the strains CECT8836 and CECT8837 at the species level in a more reliable manner, the gene 16S rDNA (Romero et al., 'Isolation and evaluation of antagonistic bacteria towards the cucurbit powdery mildew fungus Podosphaera fusca', 2004, Applied Microbiology and Biotechnology, Vol. 64, pp. 263-269) and rpoB gene (Ki et al. 'Structure of a protein-DNA complex essential for DNA protection in spores of Bacillus species', 2009, Proceedings of the National Academy of Sciences of the United States of America, Vol. 105, pp. 2806-2811) were partially sequenced. To do this, a PCR of the DNA obtained from the cultures with primers SEQ16 F-1 (SEQ ID NO: 13: GCG-GCGTGCCTAATACAT) and SEQ16 R-3 (SEQ ID NO: 14: TAAGGTTCTTCGCGTTGCTT) for 16S rDNA gene, and primers RPOBF (SEQ ID NO: 15: TCAACTAGTTCAG-TATGGACGACA) and RPOBR (SEQ ID NO: 16: ATGACAGTCGCGGTAAAACC) under standard conditions (Lane, D. J., "Nucleic acid techniques in bacterial systematics", Stackebrandt, E., and Goodfellow, M., eds., John Wiley and Sons, New York, N.Y., 1991, pp. 115-175) was performed. The PCR products were purified, conveniently concentrated and sequenced by means of an ABI PRISM™ 310 Genetic Analyzer sequencer (PE Applied Biosystems, CA, USA). The sequences obtained were analysed and aligned using BioEdit Sequencing Editor and their homology was determined using the BLAST program in the NCBI database. With this methodology the strains CECT8836 and CECT8837 were identified as B. amyloliquefaciens. Although both strains are related to other strains of the species Bacillus amyloliquefaciens, it should be noted that they are clustered into a sub-group clearly differentiated within this species when analysing the sequence corresponding to the gene rpoB (FIG. 4). This result highlights the uniqueness of the strains CECT8836 and CECT8837 with respect to other known strains of B. amyloliquefaciens.

Figure 5:
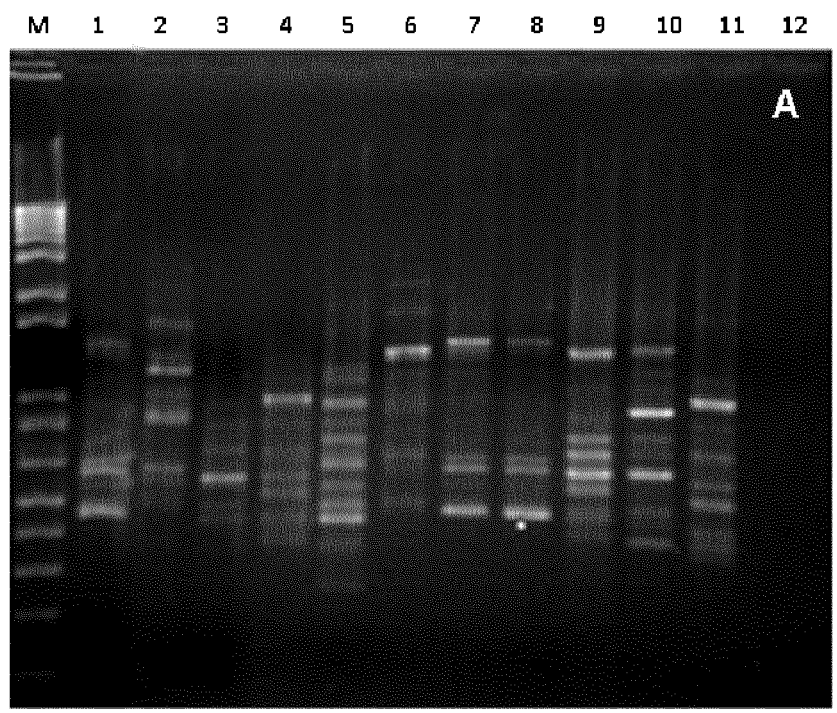
FIG. 5. Random amplification pattern of polymorphic DNA (RAPD) obtained with the primers SPASF (A) and SRFAF (B). M, molecular weight marker 1 Kb Plus (Invitrogen); 1, CECT8836; 2, CECT8837; 3, EPS2068; 4, EPS2113; 5, EPS2119; 6, EPS2128; 7, EPS2064; 8, EPS2068; 9, QST713; 10, FZB42; 11, EPS2004; 12 Negative Control.
Figure 5:
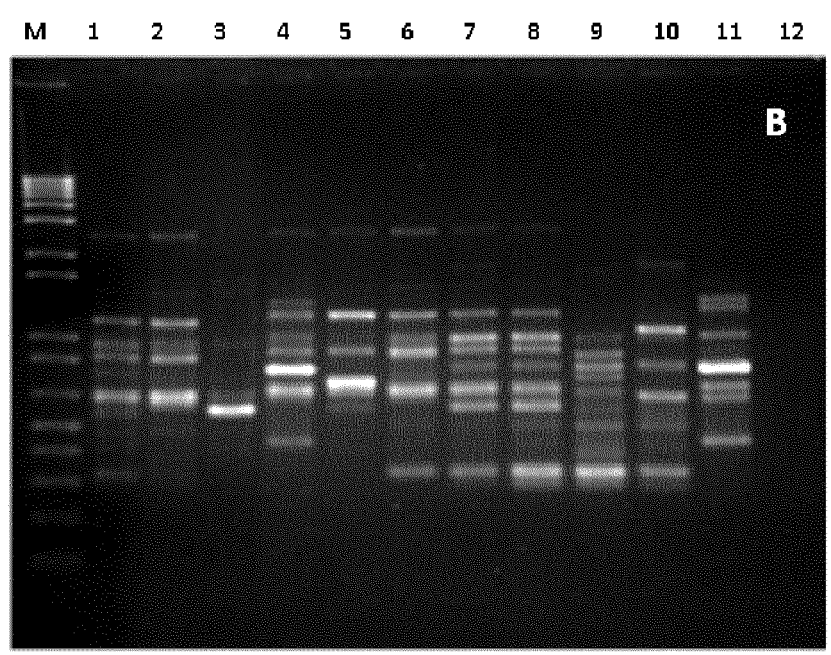

Finally, in order to differentiate the strains CECT8836 and CECT8837 of B. amyloliquefaciens from other strains of Bacillus related to the biocontrol of plant diseases, the random amplification of polymorphic DNA was performed, which is a technique known by the English acronym RAPDs (Random Amplification of Polymorphic DNA), using arbitrary short primers (8-12 nucleotides), which generate, after the PCR with a single primer, amplifications allowing for typing strains (Williams J G et al, "DNA polymorphisms amplified by arbitrary primers are useful as genetic markers", Nucleic Acids Res., 1990, vol. 18, pp. 6531-6535). This study was conducted by culturing strains in LB medium under the conditions described above, DNA extraction, and conducting PCRs with specific primers known in the state of the art and the previously described genes for the specific detection of biosynthetic genes from AMPs. The following primers were used: srfAAF (SEQ ID No: 1), srfAAR (SEQ ID No: 2), bmyBF (SEQ ID No: 3), ituCF (SEQ ID No: 5), fenDF (SEQ ID No: 7), fenDR (SEQ ID No: 8), spaSF (SEQ ID No: 9), spaSR (SEQ ID No: 10), bacAF (SEQ ID No: 11) previously described herein, and BOX-A1R (SEQ ID No: 17: CTACGGCAAGGCGCAGCTGACG) (De Clerk and De Vos. 'Genotypic diversity among *Bacillus licheniformis* strains from various sources', 2004, FEMS Microbiol Lett., Vol. 231, pp. 91-98) and RAPD-OPG 5 (SEQ ID No: 18: CTGAGACGGA) (Daffonchio et al., 'PCR fingerprinting of whole genomes: the spacers between the 16S and 23s rRNA genes and of intergenic tRNA gene regions reveal a different intraspecific genomic variability of *Bacillus cereus* and *Bacillus licheniformis*', 1998, Int J. Syst. Bacteriol., Vol. 48, pp. 107-116). The PCR mix consisted of a total volume of μl containing 1× buffer, 2 mM dNTPs, 2.5 mM $MgCl_2$, 0.4 μM primer and 0.5 U Taq polymerase (Invitrogen) and 3.5 μl of DNA (25 ng/μl). The optimized conditions for the PCR reaction were a denaturation step for 5' at 95° C.; an amplification step consisting of 5 cycles of 1' at 94° C., 1' at 40° C. and 1' at 72° C. and 30 cycles of 1' at 94° C., 1' at 60° C., and 1' at 72° C., and finally an elongation step of 5' at 72° C. In FIG. 5, it can be appreciated that strains CECT8836 and CECT8837 can be differentiated from other reference strains, such as FZB42 and QST713 and from strains randomly isolated from natural environments by using band patterns obtained with the primers srfAAF (SEQ ID No: 1) and spaSF (SEQ ID No: 9). These patterns are reproducible under the same experimental conditions for all strains and are, therefore, a very useful tool for the specific identification of the strains CECT8836 and CECT8837, and their differentiation from others of the same species.

Example 2. Culture Preparation of the Strains of the Invention for Obtaining Concentrated Cell Suspensions or Extracts from the Culture Medium The strain of the invention, preferably in the exponential growth phase, was inoculated in LB broth to a final concentration of 3%. The inoculated culture medium was incubated at 30° C. and pH 7, with stirring at 500 rpm in "batch" cultures. In bioreactor cultures oxygen concentration was 40%. In the growth stationary phase, after 24 h from the culture initiation, a cell concentration of $2.0 \times 10^9$ CFU/mL was obtained.

In order to obtain a concentrated cell suspension and the culture cell-free supernatant, the material obtained in the stationary phase was subjected to centrifugation at 8000 rpm for 15 min. The pellet containing cells and spores was resuspended in a small volume of phosphate buffer to obtain a concentrated cell suspension of $10^{10}$ CFU/mL. The cell-free supernatant resulting from centrifugation, containing the culture medium components transformed and metabolites produced by the strain, was also used for activity trials.

Example 3. Tests for Controlling Infections Caused by Phytopathogenic Bacteria in Plants by Preventive Treatments with the Strains of the Invention In order to demonstrate the efficacy of the strains of *B. amyloliquefaciens* of the invention in controlling bacterial diseases, tests with plants under controlled environment conditions in a greenhouse were carried out. The study was conducted with the 8 isolates, which showed increased production of cyclo-lipopeptides, presence of biosynthetic genes of antimicrobial peptides and broader spectrum of in vitro antagonistic activity against different bacterial pathogens. Tests were performed in 4 different pathosystems, more specifically, the capacity of the 8 strains in inhibiting infections caused by *P. syringae* pv. *syringae* and *E. amylovora* in pear trees, by *P. syringae* pv. *tomato* in tomato plants and by *X. axonopodis* pv. *vesicatoria* in pepper plants was determined.

For the tests with pear trees, self-rooted 2-year-old plants of the Conference variety were used. In this case the plants were used when they had shoots from 3 to 4 centimetres containing 5 to 6 young leaves per shoot. For the tests with tomato and pepper plants, certified seeds sown in containers of 1 L were used. The plants were used in both cases after reaching between 25 and 30 cm high. For the test with tomato plants, plants of the Rio Grande variety were used, while in the tests with pepper plants, plants of the Dulce Italiano variety were used. In all cases, treatments were performed with preventive fungicides and insecticides as well as fertilisation was performed once a week with a solution of 200 ppm NPK (20:10:20).

1—Efficacy tests were based on preventive treatments with the strains of *Bacillus*. In the tests with pear trees, both against *E. amylovora* and *P. syringae* pv. *syringae*, a double cut in the main nerve of the three leaves developed in each of the shoots was performed. Subsequently, the trees were sprayed until dripping (10 mL per tree) with the corresponding suspension of the strain of *Bacillus* at $10^{*}8$ CFU/mL (obtained in Example 2), obtained from the setting, through absorbance, of a cell suspension in Ringer solution 1/4 according to a calibration previously performed. The treated material was covered with plastic bags and kept at 25° C. for 24 h with a photoperiod of 16 h light-8 h darkness. Then, the wounds made on the leaves were inoculated with a suspension of *E. amylovora* EPS101 and *P. syringae* pv. *syringae* EPS31 at $10^{*}7$ CFU/mL (both provided by the University of Girona, Institute of Food Technology, CIDSAV) (Moragrega, C. et al. 1998. Evaluation of drench treatments with phosphonate derivatives against *Pseudomonas syringae* pv. *syringae* on pear under controlled environment conditions. European Journal of Plant Pathology 104: 171-180; Cabrefiga, J.; Montesinos, E. 2005. Analysis of aggressiveness of *Erwinia amylovora* using disease-dose and time relationships. Phytopathology. 95: 1430-1437).

2—

3—The material was reintroduced in plastic bags and kept at 25° C. in photoperiod. For the tests with tomato and pepper plants, unlike the above-mentioned tests, wounds by cutting the leaves were not performed, but they were generated during the treatment with the strains of *Bacillus* as a result of the addition of diatomaceous earth to the bacterial suspension. Thus, the treatment with the strains of *Bacillus* was made by spraying with a suspension of the strain of *Bacillus* sp. at $10^{*}8$ CFU/mL, as in the previous case, but adding diatomaceous earth (1 mg/mL) to the suspension. Treated plants were incubated at 25° C. for 24 h with a photoperiod of 16 h light-8 h darkness. Subsequently, pathogens were inoculated by spraying using a suspension adjusted at $10^{*}7$ CFU/mL *P. syringae* pv. *tomato* DC3000 for the test with tomatoes and *X. axonopodis* pv. CFBP3275 for the test with peppers.

In all tests the experimental design consisted of three repetitions of three plants per treatment with the *Bacillus* strain. Also non-treated controls, a control with a reference *Bacillus* strain (QST713) and a control treated with 100 mg/L streptomycin were performed. Two independent experiments were performed for each pathogen. The intensity of the infection was measured based on a semi-quantitative scale that was adapted for each of the pathogens because the symptoms of the infections and the infection progression are characteristics of each pathogen. For *P. syringae* pv. *syringae a scale of* 0 to 3 was used, where: 0, no symptoms; 1, necrosis located around the wound; 2, progressive necrosis in nearby nerves; and 3, necrosis in the whole leaf. For *E. amylovora* a scale of 0 to 4 was used, 0, no symptoms; 1, necrosis around the central nerve; 2, total leaf necrosis; 3, infection progression through the petiole; and 4, infection progression through the stem. For *P. syringae* pv. *tomato* a scale of 0 to 2 was used, where, 0, no symptoms; 1 presence of few necrotic wounds on the leaf; 2 high density of necrotic wounds on the leaf. Finally, for *X. axonopodis* pv. *vesicatoria* a scale of 0 to 3 was used, where: 0, no symptoms; 1, emergence of few yellow warts; 2, yellow warts affecting half of the leaf; 3, yellow warts affecting the entire leaf.

Figure 6:
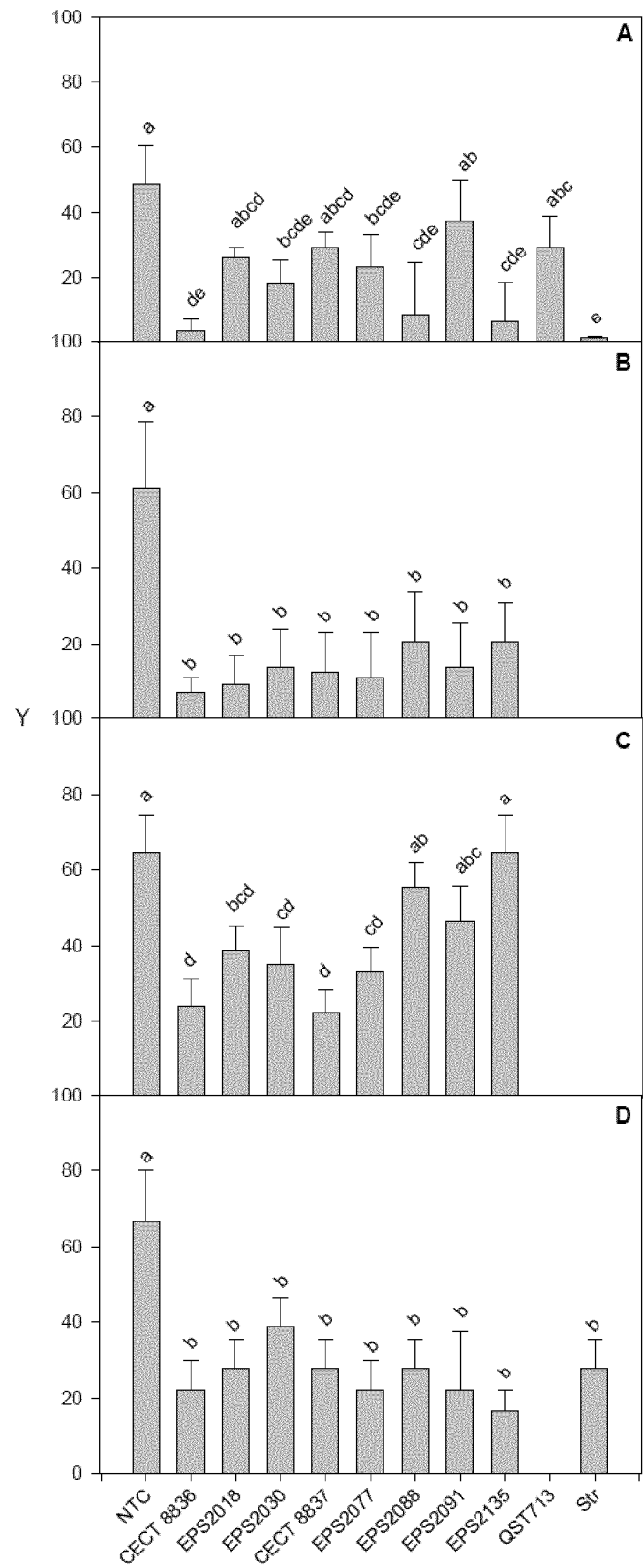
FIG. 6. Effect of treatments with different strains of *Bacillus* sp. in the intensity of infections caused by *E. amylovora* and *P. syringae* pv. *syringae* in pear trees (A and B), by *P. syringae* pv. *tomato* in tomato plants (C) and *X. axonopodis* pv. *vesicatoria* in pepper plants (D). The results are compared with a non-treated control (NTC), with a control treated with the strain QST713 of *B. amyloliquefaciens* and a control treated with the antibiotic streptomycin (Str). Values are the means of three replicates and error bars represent 95% confidence interval of the mean. Equal letters above bars indicate that the treatments do not differ significantly by Tukey test (P<0.05). Y, infection intensity (%).

In the 4 pathosystems, the strain was CECT8836, which showed a greater reduction of the infection severity. Efficiencies with respect to the non-treated control (NTC) were very high in all cases, namely 92.9% against *E. amyovora* in pear tree, 88.6% against *P. syringae* pv. *syringae* in pear tree, 62.8% against *P. syringae* pv. *tomato* in tomato and 66.7% against *X. axonopodis* pv. *vesicatoria* in pepper (FIG. 6). These efficacies were similar to those observed in the streptomycin-based control (100 mg/L) and better than those observed in the reference treatment based on the strain QST713 (for which the same protocol was followed as in Example 2) when it was included (FIG. 6A). The strain CECT8837 also stood out for its activity.

Figure 7:
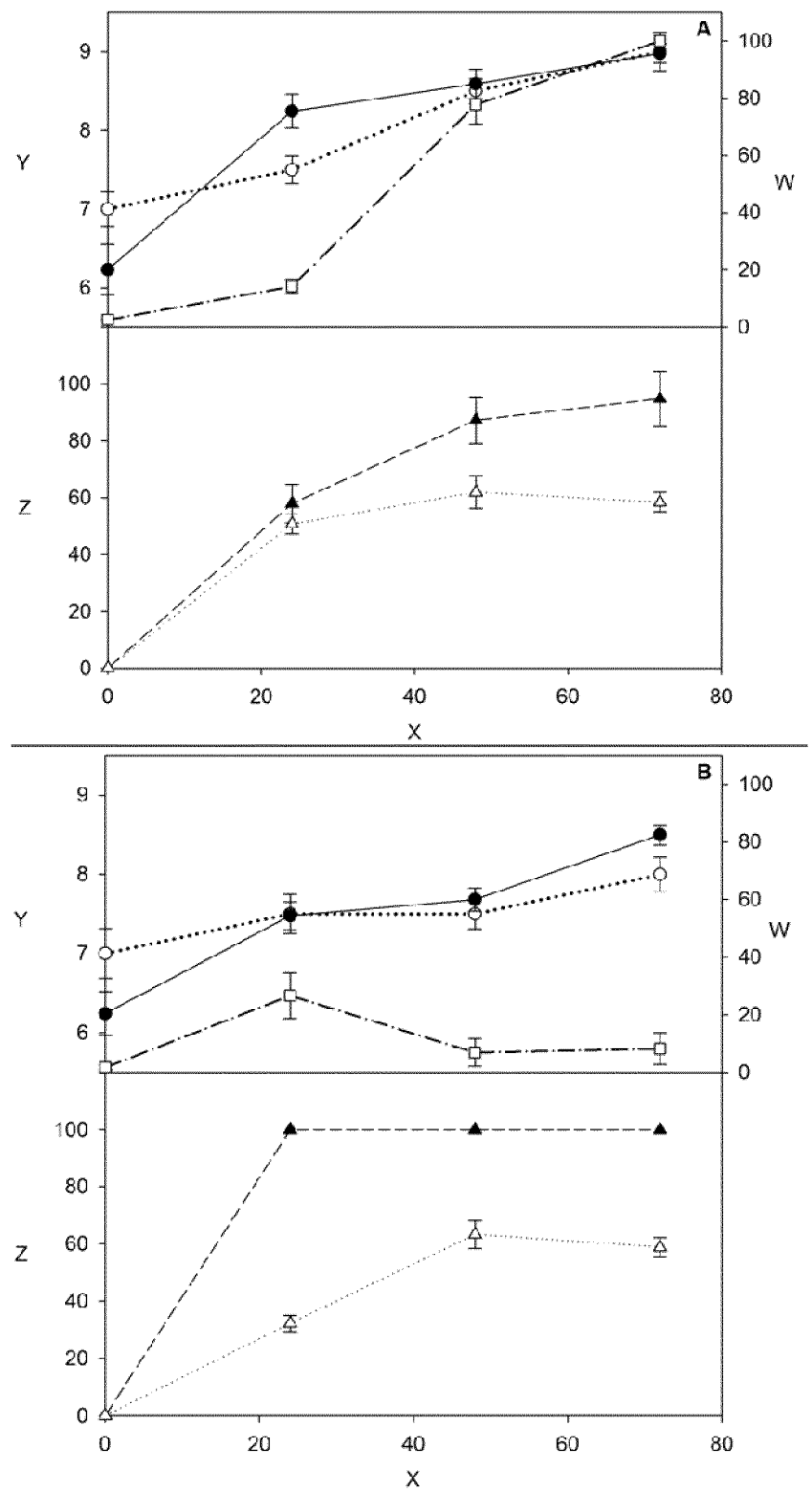
FIG. 7. Growth kinetics (●), sporulation percentage (□) and pH evolution (○) of a culture of *Bacillus amyloliquefaciens* CECT8836 in LB medium (A) and in modified saline medium (B) at 28° C., and of the antimicrobial activity of cell free extracts derived from CECT8836 supernatants against *Erwinia amylovora* (▲) and *P. syringae* pv. *syringae* (△). X, time (hours). Y, concentration of viable cells ($Log_{10}$ CFU/mL). W, sporulation (%). Z, inhibition percentage (%).

Example 4. Study of the Production of Antimicrobial Peptides in Different Culture Media and Incubation Conditions The uniqueness of the strains CECT8836 and CECT8837 highlights the interest in determining the nature of their antagonistic and inhibitory activity against different pathogens. First, it was verified that there was antimicrobial activity in the extract resulting from the "batch" growth of such strains in LB broth and in modified saline medium at 28° C., pH 7.0 and 20% $pO_2$, and how this activity varied along the cultivation process was determined. To do this, culture aliquots were taken at different times, filtered to remove the cells, lyophilised and the resulting material resuspended in water. The extract was tested using the contact test method, by applying aliquots of 20 μl extract to 180 μl a suspension adjusted to $10*8$ CFU/mL of *E. amylovora* and *P. syringae* pv. *syringae*. After 2 hours, the growth inhibition of each suspension compared to water treated control was determined. When making the growth curves in "batch" culture, in addition to the antibacterial activity, the viable cell concentration, pH and sporulation percentage were also determined (FIG. 7). It was observed that cultures grew exponentially reaching cell concentrations of about $10*9$ CFU/mL in LB broth and about $5\times10*8$ CFU/mL in saline modified medium. The growth inhibitory activity of the culture extracts against phytopathogenic bacteria began during the exponential phase and it stabilised after 48 hours of culture, already in the stationary phase. The activity against *E. amylovora* was higher in the extracts obtained from cultures in saline modified medium. As regards the activity against *P. syringae* it was similar in both cases, although the extracts obtained from cultures in LB broth were slightly more active than those obtained from cultures in modified saline medium, in contrast to the results against *E. amylovora*. These results indicate that components with high antibacterial activity are being produced during cultivation, which are differentially produced, depending on the culture medium used, and that different components are defining the activity against each one of the pathogens.

Figure 8:
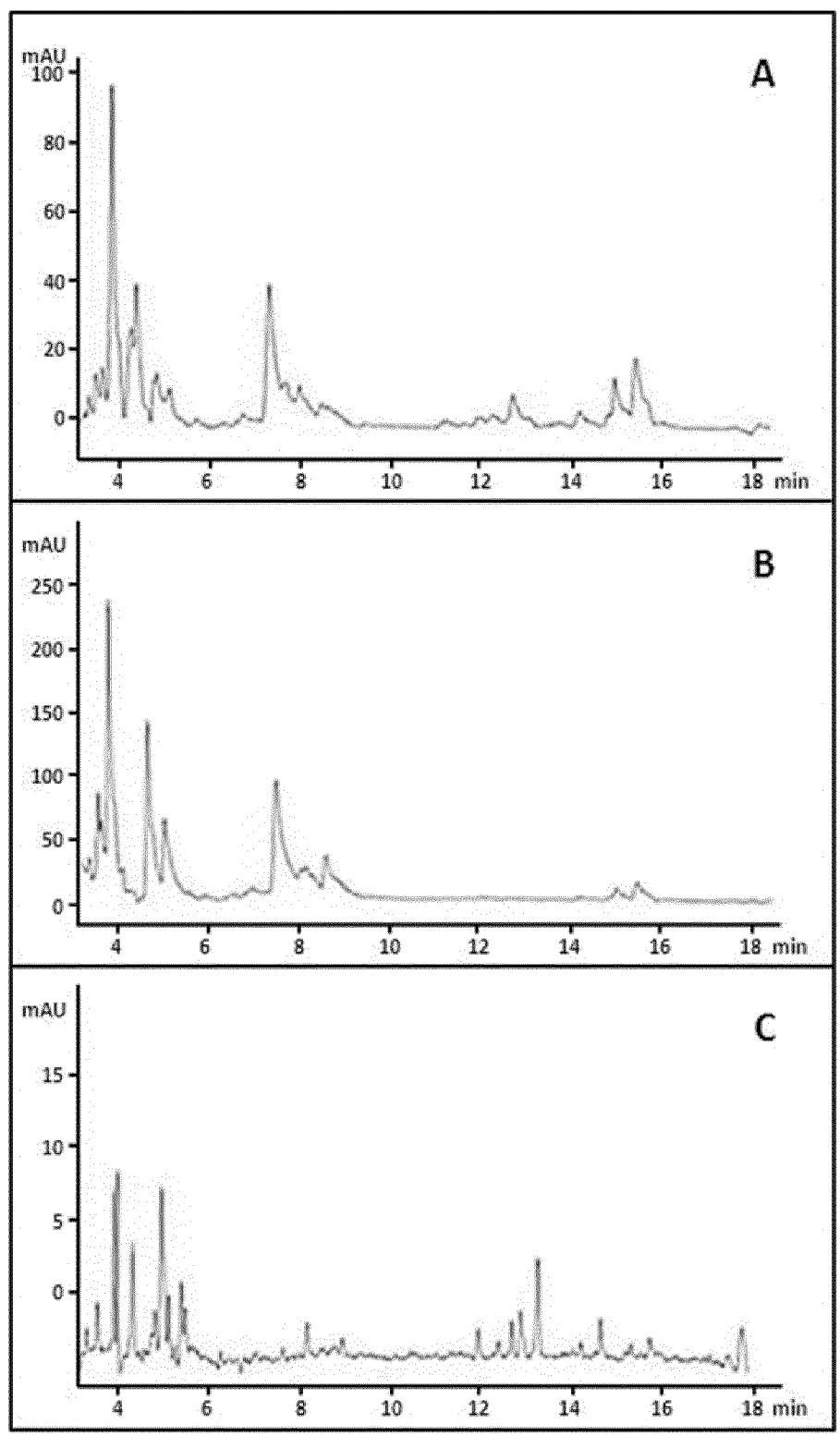
FIG. 8. Chromatographic profile resulting from the HPLC corresponding to *Bacillus* strains *CECT*8836 (A), QST713 (B) and FZB42 (C) enriched in PM liquid culture medium. In the Y axis the Absorbance for each of the collected fractions (mAU=milli-absorbance units) is represented, and in the X axis, the time at which fraction is collected (in minutes).

The culture extracts of different strains of *Bacillus*, including two reference strains, specifically FZB42 and QST713, were also analysed using HPLC on a reversed phase column as described above in Example 1 for identifying cycle-peptides. This characterisation allowed for the observation of characteristic peaks, which allow the differentiation of strain CECT8836 from the reference strains of *Bacillus* (FIG. 8). These peaks could correspond to metabolites that would be related to the antimicrobial activity exhibited by the strain CECT8836.

Example 5. Industrial Scale Production of a Composition of the Invention

For industrial scale production of compositions with the strains of the invention, optimal fermentation conditions described below using a CSTR type bioreactor in liquid medium can be used, although techniques based on solid media fermentation may also be used, all of them being standard methods used in the microbiological industry.

Figure 9:
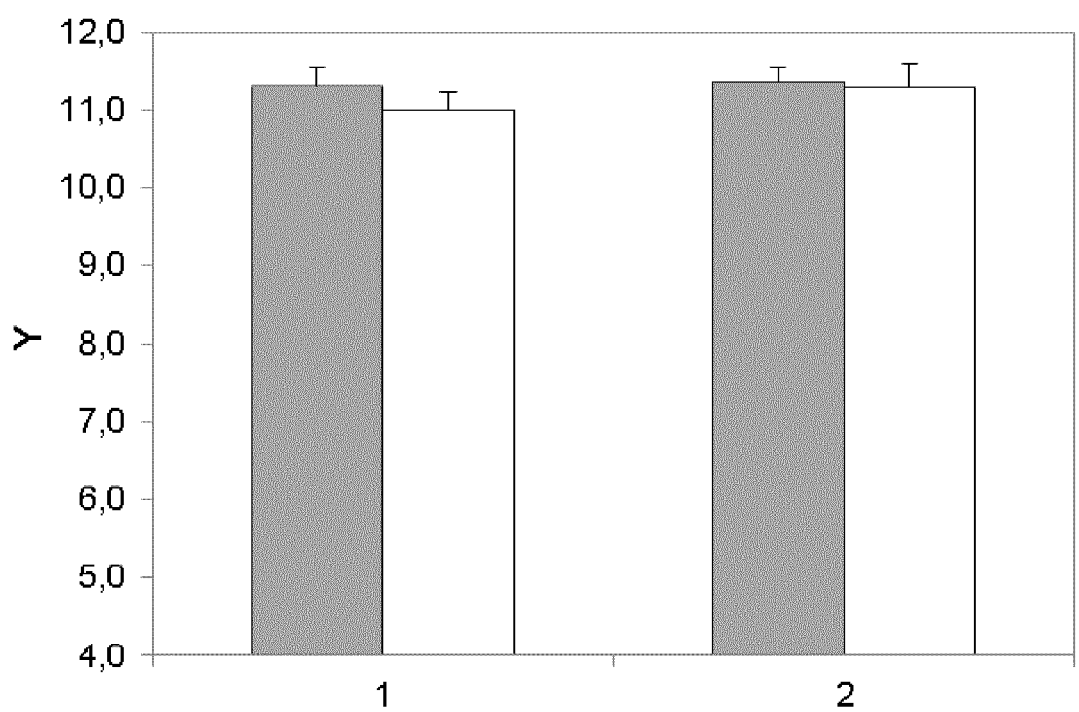
FIG. 9. Viable cells count after the fermentation process in LB medium (and after the lyophilisation process in 15% lactose (□) in two separate trials. Y axis=concentration of viable cells ($Log_{10}$ CFU/g).

In order to determine the optimal conditions, a 5-litre Braun Biostat fermenter was used in LB medium at 28° C., pH 7.0, $pO_2$ 20% ramp, and stirring at 100 rpm. An exponential culture of the *B. amyloliquefaciens* CECT8836 was inoculated at 1% and the operational parameters of the bioreactor were monitored, the growth ending in steady phase in 12 h and getting cellular concentrations of $1-2\times 10*9$ CFU/mL. Then, the culture was centrifuged in a continuous centrifuge SA-1 Westphalia—Separator at 8000 rpm and 10 l/h and the cells were collected aseptically. At the end of this step, the biomass was 10-12-fold concentrated by resuspending in phosphate buffer, obtaining about 0.5 litres of $2-4\times10*10$ CFU/mL concentrate. An inert osmotic protector ingredient (15% lactose) was added later to the concentrate and dehydrated in a Virtis lyophiliser under standard conditions for 36 h, obtaining about 40-50 g dry weight (15% active material), with a concentration of $1\times10*11$ CFU/g p.s. (FIG. 9). In such conditions a product with a cell viability close to 100%, stable, easy to store and handle is obtained, which at operational doses of $10^8$ CFU/mL allows the preparation of about 100 litres of a product ready to be applied on the crop plants to be protected. Subsequently, the material was packaged in vacuum sealed bags, and preserved at 4° C., which maintains its shelf life for more than one year.

Example 6. Colonisation of the Surface of Plants by the Strain CECT8836 Under Field Conditions The capacity of the strain CECT8836 to colonise and survive on sugar beet and cauliflower leaves under field conditions was studied. Colonization is very important to protect the main routes of entry of bacterial and fungal infections in plants. To do this, the strain CECT8836 was "batch" cultivated in LB broth at 28° C., pH 7.0, 20% $pO_2$ up to a concentration of $5\times10*9$ CFU/mL (approximately for 24 h). Cells were collected by centrifugation and resuspended in Ringer solution 1/4 to a concentration of $1\times10*8$ CFU/mL. In order to have a system for the specific analysis of the strains during the colonisation experiment and avoid the interference of autochthonous microbiota that could remain after disinfection, spontaneous mutants resistant to rifampicin (strain CECT8836R) were obtained, so that this property was used as a counter-selection tool in the viable cells counting by adding the appropriate antibiotics to the agar. These spontaneous mutants were obtained by seeding an amount of $10^9$ CFU on an agar plate containing rifampicin (100 micrograms/mL), incubating it at 30° C. for 48 h. From the rifampicin-resistant colonies that grew in such medium, one of them was purified through isolation with the "wire loop streaking" method and their identity was verified by comparing it with the wild strain CECT8836. Identity was confirmed using molecular markers (genes 16S rDNA and rpo, biosynthetic genes from antimicrobial peptides srfAA, bacA, bmyB, fenD, spaS and ituC), and in vitro activity spectrum against phytopathogen bacteria and fungi of FIG. 3.

Figure 10:
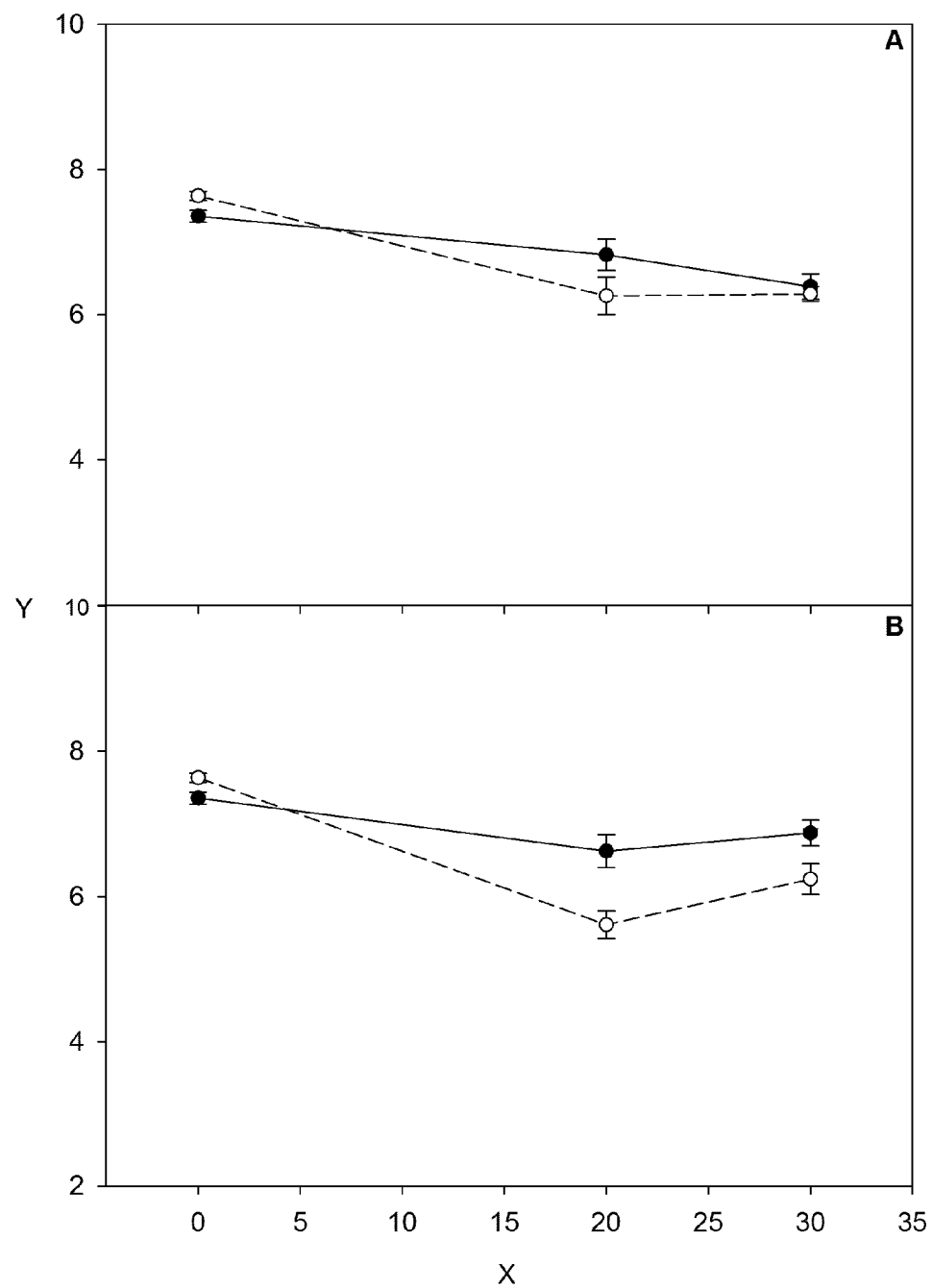
FIG. 10. Growth and survival of strain CECT8836 of *Bacillus amyloliquefaciens* (●) and of the total bacteria population in the non-treated control (○), in a commercial plot of cauliflower (A) and sugar beet (B) under field conditions. X=time (days). Y=surviving bacteria ($Log_{10}$ CFU/leaf).

Tests were performed on commercial fields located in the province of Valladolid in the case of sugar beet plants, and in the province of Valencia in the case of cauliflower plants. The experimental design consisted of 4 randomised blocks. Together with the blocks corresponding to the treatment with the strain CECT8836, the same blocks for the only water-based control treatment were included. The application of the strain CECT8836 was performed using a backpack sprayer at 10 bar pressure and 1000 L/ha application volume. Population levels were determined immediately after the application and after 20 and 30 days from the treatment. For the determination of population levels 6 leaves of different plants for each experimental block were collected and, once in the lab, the leaves corresponding to each block were homogenised jointly in neutral phosphate buffer containing peptone using a paddle stirrer. The homogenised obtained from the leaves, containing the cells of the strain CECT8836 inoculated were suitably diluted and the dilutions were seeded using an automatic coiled seeding system on LB agar plates supplemented with 100 mg/L rifampicin. For the count of total bacteria in the non-treated control, the extracts were seeded in LB without said antibiotic. Once the extracts were seeded, the plates were incubated at 28° C. for 48 h and colonies were counted through an automatic counting system. The population dynamics of the strain CECT8836 was similar both for cauliflower and sugar beet (FIG. 10). In both cases the population levels decreased in 10 and 100 times after 20 days and from then remained stable for 30 days. These results confirm the ability of the strain of the invention in the colonisation or survival in organs of plants at levels that would be sufficiently high to achieve adequate control of possible infections.

Example 7. Ability to Control Fungal and Bacterial Diseases by the Strain CECT8836 Under Field Conditions The first test under field conditions was conducted in cauliflower for the control of *Hyaloperonospora brassicae*, causing mildew. The treatment with the suspension of the strain CECT8836 consisted of the product formulated with 15% lactose resuspended in water to obtain a final concentration of 5×10*7 CFU/mL. In the test, a non-treated control and a control based on a copper-based compound applied at the concentration suggested by the manufacturer were incorporated. A total of 3 applications by spraying with strain CECT8836 were made at 20 day intervals whereas applications with the copper-based product with a rate of between 10 and 15 days were performed. The experimental design consisted of 4 randomised blocks of 15 m² with 25 plants per block. At the end of the test, the efficacy of the treatment based on the strain CECT8836 in comparison with the treatment with the copper-based compound was determined. In this test, the pathogen was not artificially inoculated, but the infections were produced by inoculum already present in the test area. The evaluation of the severity was made by calculating the percentage of foliar surface area affected by the fungal infection.

The second test under field conditions was made in sugar beets and focused on the control of *Cercospora beticola*, which cause the cercosporiosis disease or spot on the sugar beet leaf. The treatment with the suspension of the strain CECT8836 consisted of the product formulated with 15% lactose resuspended in water to obtain a final concentration of 5×10*7 CFU/mL. In the test, a non-treated control and a treatment with a copper-based compound applied at the dose suggested by the manufacturer were incorporated. A total of 3 applications with strain CECT8836 were made at 20 day intervals and 5 applications with the copper-based product with a rate of between 10 and 15 days. The experimental design consisted of 4 randomised blocks of 28 m² with 150 plants. In this case, artificial inoculation of the pathogen was also not made.

Finally, a third test was conducted under field conditions, in this case focused against a bacterium, specifically against *Erwinia amylovora*, which causes fireblight in rosaceae plants. The trial was conducted in a plot of pear trees of the Conference variety located in la Tallada d Emporda (Girona) within the Mas Badia research station. Treatments consisted of the application of the suspension of the strain CECT8836 by spraying at a dose of 10*8 CFU/mL diluted with water or with the cell-free supernatant of the culture (extract). A control treated with streptomycin (100 mg/L) and a non-treated control were also incorporated in the test.

All treatments were conducted under field conditions. After two days of treatment, the flowers treated in the field were collected and placed individually into eppendorf tubes for their inoculation under controlled laboratory conditions. Once all the flowers were placed on racks, they were inoculated with the strain EPS101 of *E. amylovora* by deposition of 10 mL of a bacterial suspension adjusted at 10*7 CFU/mL. Flowers were tightly covered with bags and incubated for 7 days at 23° C. and 100% relative humidity. After this incubation period, the intensity of the infections caused by *E. amylovora* in the flowers was determined.

Figure 11:
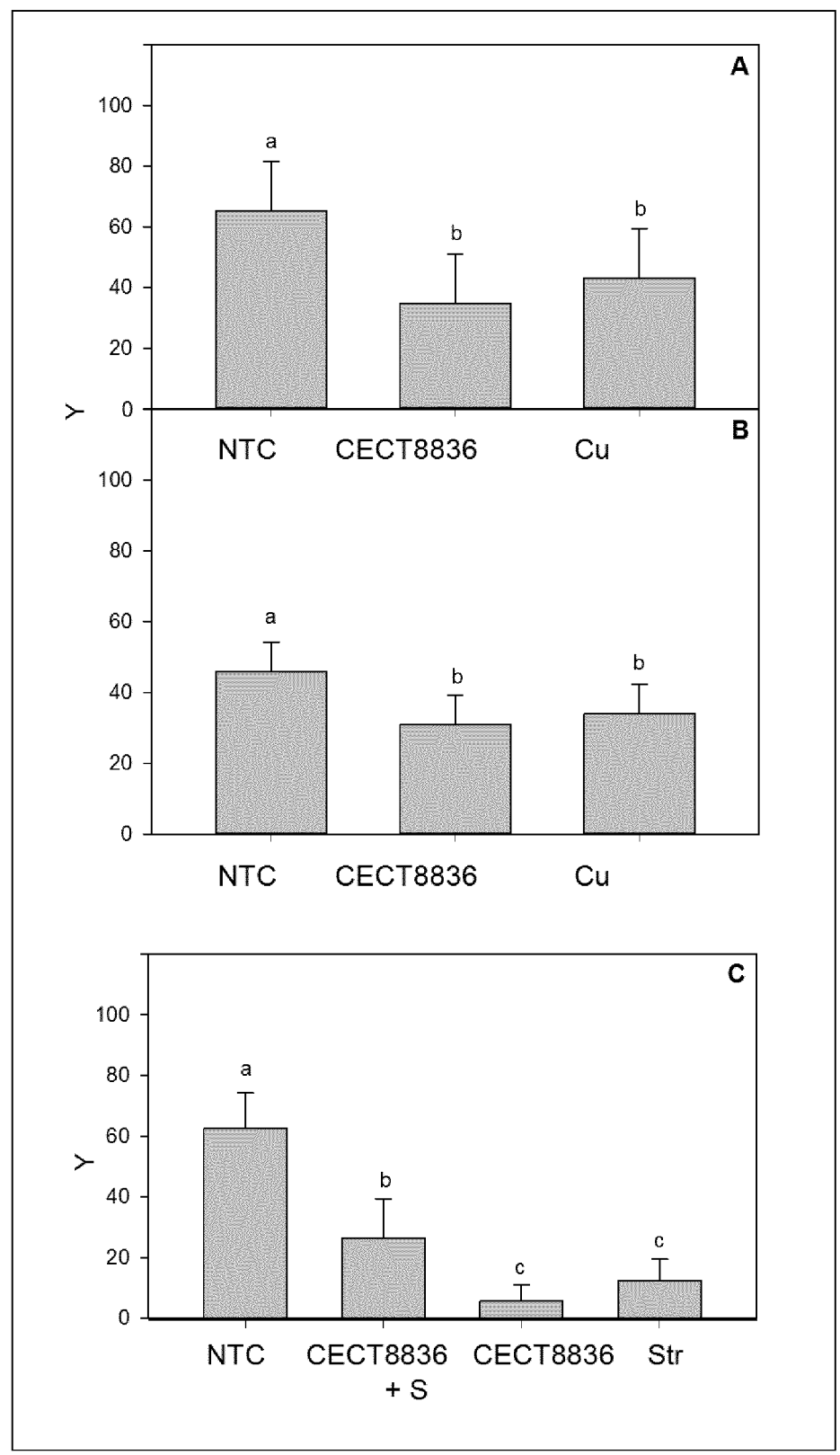
FIG. 11. Effect of treatments with the strain CECT8836 of *Bacillus amyloliquefaciens* alone (CECT8836) or together with the culture extract (CECT8836+S) in the reduction of the intensity of infections caused by *Hyaloperonospora brassicae* in cauliflower plants (A), by *Cercospora beticola* in beet plants (B) and by *Erwinia amylovora* in pear trees (C). The results are compared with a non-treated control (NTC) and a control treated with a reference product, a copper compound (Cu) in the control trials against fungi, and with the antibiotic streptomycin (Str) in the trial against the bacterium. Values are the means of three replicates and error bars represent 95% confidence interval of the mean. Equal letters above bars indicate that the treatments do not differ significantly by Tukey test (P<0.05). Y, infection intensity (%).

In the three tests, it was observed that the strain CECT8836 significantly reduced the intensity of the infections caused by the 3 pathogens (FIG. 11). In the case of fungi, specifically *H. brassicae* and *Cercospora beticola*, the treatment with strain CECT8836 not only significantly reduced the severity of the infections, but also presented efficacy levels similar to those observed in treatments with copper-based products. In the case of the test against *E. amylovora* in pear trees, it was observed that the strain CECT8836 based treatments significantly reduced the severity of the infections caused by *E. amylovora* in the flowers compared to the non-treated control. Furthermore, strain CECT8836 based treatments presented an efficacy similar or greater than that observed with the standard treatment with streptomycin. It should be noted that the treatment consisting of the strain CECT8836 diluted with the extract of the cell-free culture, presented a very high efficacy, even higher than that presented by the treatment with streptomycin, which highlights the existence of metabolites with antibacterial activity in the growth extract that enhances the activity of the strain alone.

The invention claimed is:

1. A pesticide, wherein the pesticide comprises a *Bacillus amyloquefaciens* strain selected from CECT8836 strain and/or a mutant CECT8836 strain at a concentration from $10^7$ cfu/g to $10^{10}$ cfu/g, wherein said mutant strain is obtained using the strain CECT8836 of *Bacillus amyloliquefaciens* and also maintains the following features of the starting strain:

antagonistic activity of the starting strain against the bacteria *Erwinia amylovora, Pseudomonas syringae* pv *syringae, P. syringae* pv tomato, *Xanthomonas axonopodis* pv *vesicatoria, X. arboricola* pv *fragariae, Clavibacter michiganensis* subsp. *michiganensis, Ralstonia solanacearum, Rhizobium radiobacter, Pectobacterium carotovorum*, and against the fungi *Phytophthora cinnamomi, P. cactorum, Penicillium expansum, Botrytis cinerea, Fusarium oxysporum*, and *Pytium ultimum*; and an ability to colonise and survive in an aerial part of a plant; and production of lipopeptides surfactin, bacillomicin, iturin, and fengycin, the lantibiotic subtilin, and the dipeptide bacilysin.

2. The pesticide of claim 1, wherein the CECT8836 strain and/or mutant CECT8836 strain is in the form of a cell free extract.

3. The pesticide of claim 1, wherein the pesticide further comprises one or more agriculturally acceptable compounds.

4. The pesticide of claim 3, wherein the one or more agriculturally acceptable compounds is selected from the group consisting of plant strengtheners, nutrients, wetting agents, compounds that improve adherence, buffering compounds, stabilisers, antioxidants, osmotic protectors and sunscreens.

5. The pesticide of claim 1, further comprising at least one additional pesticide.

6. The pesticide of claim 5, wherein the at least one additional pesticide comprises a bacterial strain with antifungal and/or antibacterial activity, a fungicide, an insecticide, and/or a nematicide.

7. The pesticide of claim 6, wherein the at least one additional pesticide comprises a CECT8837 and/or mutant CECT8837 strain.

8. A method of producing a cell-free extract from the strain CECT8836 of *Bacillus amyloliquefaciens* or a mutant thereof as defined in claim 1, comprising:

(i) inoculating a *B. amyloliquefaciens* strain in a suitable culture medium, (ii) subjecting the culture medium to suitable growth conditions, (iii) separating cells from the culture medium, and (iv) collecting the cell-free extract.

9. The method of claim 8, further comprising subjecting the cell-free extract to a concentration process.

10. The method of claim 9, wherein the concentration process is dehydration, filtration, ultra-filtration, precipitation, centrifugation, and/or chromatography.

11. The method of claim 10, wherein dehydration occurs by lyophilisation and/or spray drying.

12. The method of claim 8, wherein the suitable conditions comprise one or more of a temperature between 25° C. to 35° C., a pH of between 6 and 9, and an oxygen concentration of between 10 to 50%.

13. The method of claim 8, wherein appropriate growth conditions comprise stirring.

14. The method of claim 8, wherein cells are separated from the culture medium to obtain a concentrated suspension.

15. A cell-free extract derived from the strain CECT8836 of *Bacillus amyloliquefaciens* or a mutant thereof obtainable by the process as defined in claim 8.

16. A method of controlling a disease caused by a bacterium or fungus in a plant that is a crop of interest, comprising administering the pesticide as defined in claim 1 to the plant.

17. A method of controlling a disease caused by a bacterium or fungus in a plant that is a crop of interest, comprising administering the cell extract of claim 15 to the plant.

* * * * *